US012195727B2

(12) United States Patent
Li et al.

(10) Patent No.: US 12,195,727 B2
(45) Date of Patent: Jan. 14, 2025

(54) *PSEUDOMONAS* STRAINS AND RELATED METHODS

(71) Applicants: Agriculture Victoria Services PTY LTD, Bundoora (AU); Dairy Australia Limited, Southbank (AU); Geoffrey Gardiner Dairy Foundation Limited, Melbourne (AU)

(72) Inventors: Tongda Li, Southbank (AU); Ian Ross Tannenbaum, Bundoora (AU); Jatinder Kaur, Taylors Hill (AU); Christian Krill, Reservoir (AU); Timothy Ivor Sawbridge, Coburg (AU); Ross Mann, Coburg (AU); German Carlos Spangenberg, Bundoora (AU)

(73) Assignees: Agriculture Victoria Services PTY LTD, Victoria (AU); Dairy Australia Limited, Victoria (AU); Geoffrey Gardiner Dairy Foundation Limited, Victoria (AU)

( * ) Notice: Subject to any disclaimer, the term of this patent is extended or adjusted under 35 U.S.C. 154(b) by 417 days.

(21) Appl. No.: 17/627,789

(22) PCT Filed: Jul. 17, 2020

(86) PCT No.: PCT/AU2020/050736
§ 371 (c)(1),
(2) Date: Jan. 17, 2022

(87) PCT Pub. No.: WO2021/011999
PCT Pub. Date: Jan. 28, 2021

(65) Prior Publication Data
US 2023/0193193 A1    Jun. 22, 2023

(30) Foreign Application Priority Data

Jul. 19, 2019 (AU) .............................. 2019902560

(51) Int. Cl.
*C12N 1/20* (2006.01)
*A01H 3/00* (2006.01)
*A01H 17/00* (2006.01)
*A01N 63/27* (2020.01)
*C12R 1/38* (2006.01)

(52) U.S. Cl.
CPC .............. *C12N 1/205* (2021.05); *A01H 3/00* (2013.01); *A01H 17/00* (2013.01); *A01N 63/27* (2020.01); *C12R 2001/38* (2021.05)

(58) Field of Classification Search
None
See application file for complete search history.

(56) References Cited

U.S. PATENT DOCUMENTS

2020/0178540 A1    6/2020    Dagher et al.

FOREIGN PATENT DOCUMENTS

| CN | 108467839 A | 8/2018 |
| CN | 109 566 655 A | 4/2019 |
| WO | 2019/023226 A1 | 1/2019 |

OTHER PUBLICATIONS

Vyas et al. BMC Microbiol 9, 174 (2009). https://doi.org/10.1186/1471-2180-9-174.*
Gupta et al. Sustainable Agriculture Reviews. Sustainable Agriculture Reviews, vol. 11. Springer, Dordrecht. https://doi.org/10.1007/978-94-007-5449-2_8 Oct. 25, 2012.*
Behrendt et al. International Journal of Systemic and Evolutionary Microbiology (2003), 53, 1461-1469.*
Nutrient Broth II retrieved from http://biotrading.com/assets/productinformatie/sifin/tds/tn1174-pi-en_2016_06_21_15_25.pdf dated Mar. 20, 2014.*
Behrendt, U. et al. "Fluorescent pseudomonads associated with the phyllosphere of grasses; *Pseudomonas trivialis* sp. nov., *Pseudomonas poae* sp. nov. and *Pseudomonas congelans* sp. nov." International Journal of Systematic and Evolutionary Microbiology, 2003, pp. 1461-1469, vol. 53, No. 5.
Cho, K. et al. Endophytic bacterial communities in Ginseng and their Antifungal Activity Against Pathogens Microbial Ecology, 2007, pp. 341-351, vol. 54, No. 2.
Ghosh, R. et al. "Biological control of Alternaria alternata causing leaf spot disease of Aloe Vera using two strains of rhizobacteria", Biological Control, 2016, pp. 102-108, vol. 97.
Irshad, U. et al. "Bacterial Subspecies Variation and Nematode Grazing Change P Dynamics in the Wheat Rhizosphere", Frontiers in Microbiology, 1990, pp. 1-11, vol. 9.
Verma, P. et al. "Appraisal of diversity and functional attribute of thermotolerant wheat associated bacteria from the peninsular zone of India", Saudi Journal of Biological Sciences, 2016, pp. 1882-1895, vol. 26, No. 7.
Vyas, P. et al. "Organic acid production in vitro and plant growth promotion in maize underphosphate-solubilizing fluorescent Pseudomonas", BMC Microbiology, 2009, pp. 1-15, vol. 9, No. 174.
Ankenbrand, M. et al. " AliTV-interactive visualization of whole genome comparisons", PeerJ Comput. Sci., 2017, pp. 1-11, vol. 3.
Bolger, A. et al. "Trimmomatic: a flexible trimmer for Illumina sequence data", Bioinformatics, 2014, pp. 2114-2120, vol. 30, No. 15.
Chun, J. et al. "Proposed minimal standards for the use of genome data for the taxonomy of prokaryotes", International Journal of Systematic and Evolutionary Microbiology, 2018, pp. 461-466, vol. 68.

(Continued)

*Primary Examiner* — Oluwatosin A Ogunbiyi
(74) *Attorney, Agent, or Firm* — Anderson Patent Law Firm

(57) ABSTRACT

The present invention relates to an endophyte strain isolated from a plant of the Poaceae family, wherein said endophyte is a strain of *Pseudomonas poae* which provides bioprotection and/or biofertilizer phenotypes to plants into which it is inoculated. The present invention also relates to plants infected with the endophyte and related methods.

20 Claims, 15 Drawing Sheets

Figure 2:
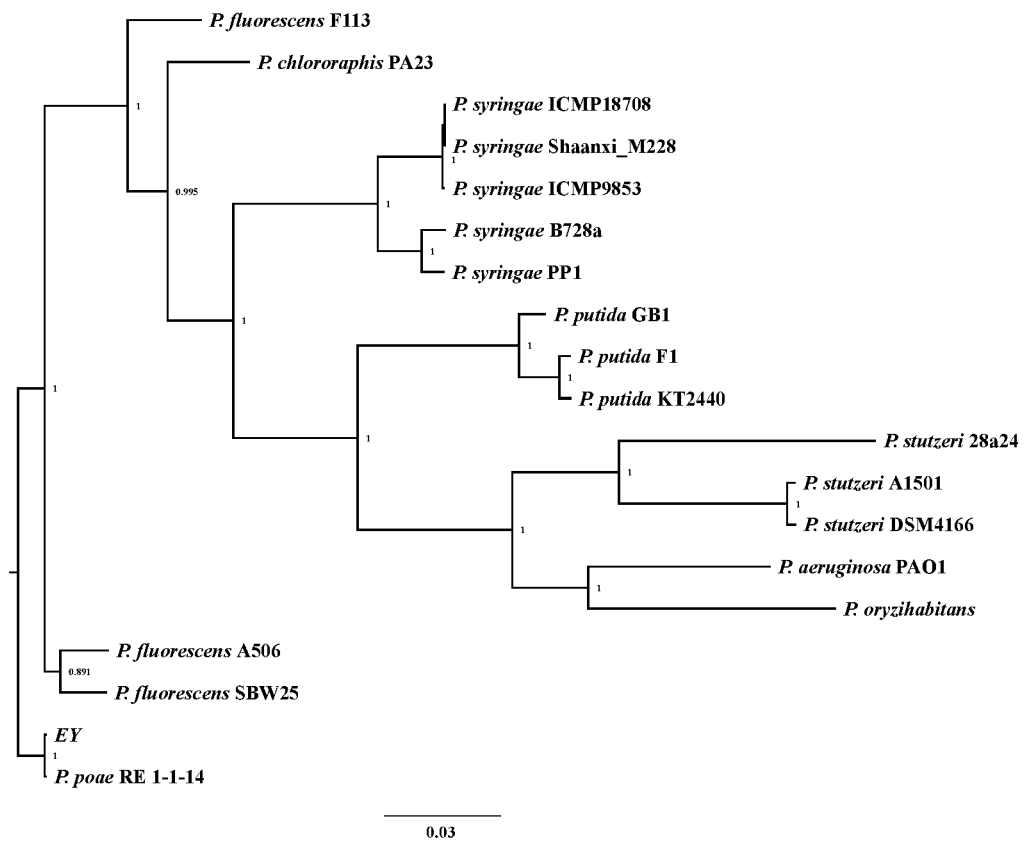

Specification includes a Sequence Listing.

(56) References Cited

OTHER PUBLICATIONS

De Coster, W. et al. "NanoPack: visualizing and processing long-read sequencing data", Bioinformatics, 2018, pp. 2666-2669, vol. 34, No. 15.

Henry, E. et al. "Direct and Indirect Visualization of Bacterial Effector Delivery into Diverse Plant Cell Types during Infection", The Plant Cell, 2017, pp. 1555-1570, vol. 29.

Li, H. et al. "Minimap2: pairwise alignment for nucleotide sequences", Bioinformatics, 2018, pp. 3094-3100, vol. 34, No. 18.

Li, Q. et al., GENBANK Accession No. MG835948.1, Pseudomonas poae strain HTM601-1 16S ribosomal RNA gene, partial sequence, Feb. 9, 2019.

Li, Q. et al., GENBANK Accession No. MG835959.1, Pseudomonas poae strain HTM603-3 16S ribosomal RNA gene, partial sequence, Feb. 9, 2019.

Li, Q. et al., GENBANK Accession No. MG835996.1, Pseudomonas poae strain HTI604-2 16S ribosomal RNA gene, partial sequence, Feb. 9, 2019.

Li, Q. et al., GENBANK Accession No. MG836002.1, Pseudomonas poae strain HTI605-4 16S ribosomal RNA gene, partial sequence, Feb. 9, 2019.

Lindeberg, M. et al. "Pseudomonas syringae type III effector repertoires: last words in endless arguments", Cell Press, 2012, pp. 199-208, vol. 20, No. 4.

Löytynoja, A. et al. "Phylogeny-aware alignment with PRANK", Multiple Sequence Alignment Methods, Methods in Molecular Biology, pp. 155-170, vol. 1079, 2014.

Müller, H. et al. "Complete Genome Sequence of the Sugar Beet Endophyte Pseudomonas poae RE*1-1-14, a disease-Suppressive Bacterium", Genome Announcements, 2013, pp. 1-2, vol. 1, Issue 2.

Page, A. et al. "Roary: rapid large-scale prokaryote pan genome analysis", Bioinformatics, 2015, pp. 3691-3693, vol. 31, No. 22.

Price, M. et al. FastTree 2—Approximately Maximum-Likilihood Trees for Large Alignments, PLOS One, Mar. 2010, pp. 1-10, vol. 5, Issue 3.

Sundara Rao, W.V.B. et al. "Phosphate Dissolving Micro-Organisms in the Soil and Rhizosphere", Indian Agricultural Research Institute, 1963, pp. 272-278, vol. 33, No. 7.

Richter, M. et al. "Shifting the genomic gold standard for the prokaryotic species definition", PNAS, 2009, pp. 19126-19131, vol. 106, No. 45.

Rodiguez, H. et al. "Phosphate solubilizing bacteria and their role in plant growth promotion", Biotechnolgy Advances, 1999, pp. 319-339, vol. 17.

Seemann, T. et al. "Prokka: rapid prokaryotic genome annotation", Bioinformatics, 2014, pp. 2068-2069, vol. 30, No. 14.

Sharma, S. et al. "Phosphate solubilizing microbes: sustainable approach for managing phosphorus deficiency in agricultural soils" SpringerPlus, 2013, pp. 1-14, vol. 2, No. 587.

Sun, H. et al. "Benefits of Pseudomonas poae s61 on Astragalus mongholicus growth and bioactive compund accumulation under drought stress", Journal of Plant Interactions, 2019, pp. 205-212, vol. 14, No. 1.

Tallapragada, J. et al. "Phosphate-solubilizing microbes and their occurrence in the rhizospheres of Piper betel in Karnataka, India", Turk. J. Biol., 2012, pp. 25-35, vol. 36.

Vaser, R. et al. "Fast and accurate de novo genome assembly from long uncorrected reads", Genome Research, 2017, pp. 737-746, vol. 27.

Walker, B. et al. "Pilon: An integrated Tool for Comprehensive Microbial Variant Detection and Genome Assembly Improvement", PLOS One, 2014, pp. 1-14, vol. 9, Issue 11.

Weber, T. et al. "antiSMASH 3.0—a comprehensive resource for the genome mining of biosynthetic gene clusters", Nucleic Acids Research, 2015, pp. W237-W243, vol. 43.

Wei, H. et al. "Modular Study of the Type III Effector Repertoire in *Pseudomonas syringae* pv. tomato DC3000 Reveals a Matrix of Effector Interplay in Pathogenesis", Cell Reports, 2018, pp. 1630-1638, vol. 23.

Wick, R. et al. "Bandage: interactive visualization of de novo genome assemblies" Bioinformatics, 2015, pp. 3350-3352, vol. 31, No. 20.

Wick, R. et al. "Unicycler: Resolving bacterial genome assemblies from short and long sequencing reads", PLOS Computational Biology, 2017, pp. 1-22, vol. 13, No. 6.

Zachow, C. et al. "The Novel Lipopeptide Poaeamide of the Endophyte Pseudomonas poae RE*1-1-14 is involved in Pathogen Suppression and Root Colonization" Molecular Plant-Microbe Interactions, 2015, pp. 800-810, vol. 28, No. 7.

* cited by examiner

TGCCTAGGAATCTGCCTGGTAGTGGGGGATAACGTTCGGAAACGGACGCTAATACCGCATACGTCCTACGG
GAGAAAGCAGGGGACCTTCGGGCCTTGCGCTATCAGATGAGCCTAGGTCGGATTAGCTAGTTGGTGGGGTA
ATGGCTCACCAAGGCGACGATCCGTAACTGGTCTGAGAGGATGATCAGTCACACTGGAACTGAGACACGGT
CCAGACTCCTACGGGAGGCAGCAGTGGGGAATATTGGACAATGGGCGAAAGCCTGATCCAGCCATGCCGCG
TGTGTGAAGAAGGTCTTCGGATTGTAAAGCACTTTAAGTTGGGAGGAAGGGCAGTTACCTAATACGTGATTG
TTTTGACGTTACCGACAGAATAAGC\ACCGGCTAACTCTGTGCCAGCAGCCGCGGTAATACAGAGGGTGCAA
GCGTTAATCGGAATTACTGGGCGTAAAGCGCGCGTAGGTGGTTTGTTAAGTTGGATGTGAAATCCCCGGGC
TCAACCTGGGAACTGCATTCAAAACTGACTGACTAGAGTATGGTAGAGGGTGGTGGAATTTCCTGTGTAGCG
GTGAAATGCGTAGATATAGGAAGGAACACCAGTGGCGAAGGCGACCACCTGGACTAATACTGACACTGAGG
TGCGAAAGCGTGGGGAGCAAACAGGATTAGATACCCTGGTAGTCCACGCCGTAAACGATGTCAACTAGCCG
TTGGAAGCCTTGAGCTTTTAGTGGCGCAGCTAACGCATTAAGTTGACCGCCTGGGGAGTACGGCCGCAAGG
TTAAAACTCAAATGAATTGACGGGGGCCCGCACAAGCGGTGGAGCATGTGGTTTAATTCGAAGCAACGCGA
AGAACCTTACCAGGCCTTGACATCCAATGAACTTTCTAGAGATAGATTGGTGCCTTCGGGAACATTGAGACA
GGTGCTGCATGGCTGTCGTCAGCTCGTGTCGTGAGATGTTGGGTTAAGTCCCGTAACGAGCGCAACCCTTGT
CCTTAGTTACCAGCACGTCATGGTGGGCACTCTAAGGAGACTGCCGGTGACAAACCGGAGGAAGGTGGGGA
TGACGTCAAGTCATCATGGCCCTTACGGCCTGGGCTACACACGTGCTACAATGGTCGGTACAGAGGGTTGCC
AAGCCGCGAGGTGGAGCTAATCCCATAAAACCGATCGTAGTCCGGATCGCAGTCTGCAACTCGACTGCGTG
AAGTCGGAATCGCTAGTAATCGCGAATCAGAATGTCGCGGTGAATACGTTCCCGGGCCTTGTACAC

Figure 1

A. *poaA* Gene Cluster
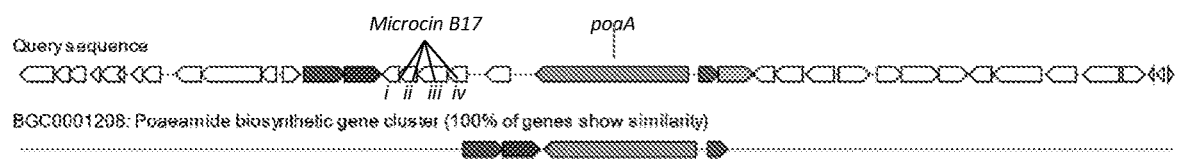
B. *poaB* and *poaC* Gene Cluster
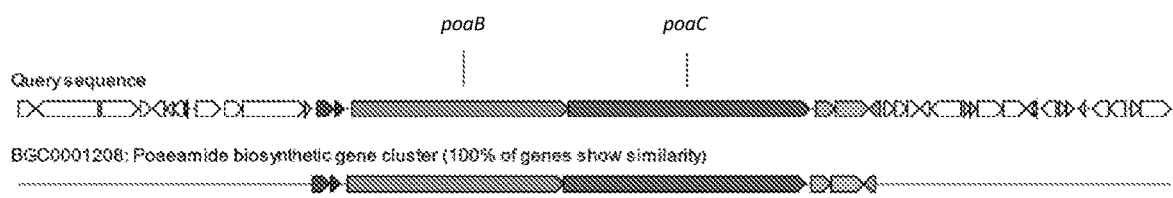
Figure 4

SEQUENCE LISTING

```
<160> NUMBER OF SEQ ID NOS: 5

<210> SEQ ID NO 1
<211> LENGTH: 1278
<212> TYPE: DNA
<213> ORGANISM: Pseudomonas poae

<400> SEQUENCE: 1
tgcctaggaa tctgcctggt agtgggggat aacgttcgga aacggacgct aataccgcat      60
acgtcctacg ggagaaagca ggggaccttc gggccttgcg ctatcagatg agcctaggtc     120
ggattagcta gttggtgggg taatggctca ccaaggcgac gatccgtaac tggtctgaga     180
ggatgatcag tcacactgga actgagacac ggtccagact cctacgggag gcagcagtgg     240
ggaatattgg acaatgggcg aaagcctgat ccagccatgc cgcgtgtgtg aagaaggtct     300
tcggattgta aagcacttta agttgggagg aagggcagtt acctaatacg tgattgtttt     360
gacgttaccg acagaataag caccggctaa ctctgtgcca gcagccgcgg taatacagag     420
ggtgcaagcg ttaatcggaa ttactgggcg taaagcgcgc gtaggtggtt tgttaagttg     480
gatgtgaaat ccccgggctc aacctgggaa ctgcattcaa aactgactga ctagagtatg     540
```

```
gtagagggtg gtggaatttc ctgtgtagcg gtgaaatgcg tagatatagg aaggaacacc        600
agtggcgaag gcgaccacct ggactaatac tgacactgag gtgcgaaagc gtggggagca        660
aacaggatta gataccctgg tagtccacgc cgtaaacgat gtcaactagc cgttggaagc        720
cttgagcttt tagtggcgca gctaacgcat taagttgacc gcctgggag tacggccgca         780 aggttaaaac tcaaatgaat tgacggggc ccgcacaagc ggtggagcat gtggtttaat         840
tcgaagcaac gcgaagaacc ttaccaggcc ttgacatcca atgaactttc tagagataga        900
ttggtgcctt cgggaacatt gagacaggtg ctgcatggct gtcgtcagct cgtgtcgtga        960
gatgttgggt taagtcccgt aacgagcgca acccttgtcc ttagttacca gcacgtcatg       1020
gtgggcactc taaggagact gccggtgaca aaccggagga aggtggggat gacgtcaagt       1080
catcatggcc cttacggcct gggctacaca cgtgctacaa tggtcggtac agagggttgc       1140
caagccgcga ggtggagcta atcccataaa accgatcgta gtccggatcg cagtctgcaa       1200
ctcgactgcg tgaagtcgga atcgctagta atcgcgaatc agaatgtcgc ggtgaatacg       1260
ttcccgggcc ttgtacac                                                    1278

<210> SEQ ID NO 2
<211> LENGTH: 20
<212> TYPE: DNA
<213> ORGANISM: Artificial Sequence
<220> FEATURE:
<223> OTHER INFORMATION: Primer

<400> SEQUENCE: 2
agagtttgat cmtggctcag                                                    20

<210> SEQ ID NO 3
<211> LENGTH: 19
<212> TYPE: DNA
<213> ORGANISM: Artificial Sequence
<220> FEATURE:
<223> OTHER INFORMATION: Primer

<400> SEQUENCE: 3
ggttaccttg ttacgactt                                                     19

<210> SEQ ID NO 4
<211> LENGTH: 20
<212> TYPE: DNA
<213> ORGANISM: Artificial Sequence
<220> FEATURE:
<223> OTHER INFORMATION: Primer

<400> SEQUENCE: 4
tgttaaacac gcaactcgcc                                                    20

<210> SEQ ID NO 5
<211> LENGTH: 22
<212> TYPE: DNA
<213> ORGANISM: Artificial Sequence
<220> FEATURE:
<223> OTHER INFORMATION: Primer

<400> SEQUENCE: 5
aaaggtgcac tcacaacctc tg                                                 22
```

PSEUDOMONAS STRAINS AND RELATED METHODS

FIELD OF THE INVENTION

The present invention relates to novel plant microbiome strains, plants infected with such strains and related methods.

BACKGROUND OF THE INVENTION

Microbes represent an invaluable source of novel genes and compounds that have the potential to be utilised in a range of industrial sectors. Scientific literature gives numerous accounts of microbes being the primary source of antibiotics, immune-suppressants, anticancer agents and cholesterol-lowering drugs, in addition to their use in environmental decontamination and in the production of food and cosmetics.

A relatively unexplored group of microbes known as endophytes, which reside e.g. in the tissues of living plants, offer a particularly diverse source of novel compounds and genes that may provide important benefits to society, and in particular, agriculture.

Endophytes may be fungal or bacterial. Endophytes often form mutualistic relationships with their hosts, with the endophyte conferring increased fitness to the host, often through the production of defence compounds. At the same time, the host plant offers the benefits of a protected environment and nutriment to the endophyte.

Important forage grasses perennial ryegrass (*Lolium perenne*) are commonly found in association with fungal and bacterial endophytes. However, there remains a general lack of information and knowledge of the endophytes of these grasses as well as of methods for the identification and characterisation of novel endophytes and their deployment in plant improvement programs.

Knowledge of the endophytes of perennial ryegrass may allow certain beneficial traits to be exploited in enhanced pastures, or lead to other agricultural advances, e.g. to the benefit of sustainable agriculture and the environment.

There exists a need to overcome, or at least alleviate, one or more of the difficulties or deficiencies associated with the prior art.

SUMMARY OF THE INVENTION

In one aspect, the present invention provides a substantially purified or isolated endophyte strain isolated from a plant of the Poaceae family, wherein said endophyte is a strain of *Pseudomonas poae* which provides bioprotection and/or biofertilizer phenotypes to plants into which it is inoculated. In a preferred embodiment, the *Pseudomonas poae* strain may be strain EY as described herein and as deposited with The National Measurement Institute of 1/153 Bertie Street, Port Melbourne, VIC 3207, Australia on 17 May 2019 with accession number V19/009907.

As used herein the term "endophyte" is meant a bacterial or fungal strain that is closely associated with a plant. By "associated with" in this context is meant that the bacteria or fungus lives on, in or in close proximity to a plant. For example, it may be endophytic, for example living within the internal tissues of a plant, or epiphytic, for example growing externally on a plant.

As used herein the term "substantially purified" is meant that an endophyte is free of other organisms. The term includes, for example, an endophyte in axenic culture.

Preferably, the endophyte is at least approximately 90% pure, more preferably at least approximately 95% pure, even more preferably at least approximately 98% pure, even more preferably at least approximately 99% pure.

As used herein the term 'isolated' means that an endophyte is removed from its original environment (e.g. the natural environment if it is naturally occurring). For example, a naturally occurring endophyte present in a living plant is not isolated, but the same endophyte separated from some or all of the coexisting materials in the natural system, is isolated.

As used herein the term "bioprotection and/or biofertilizer" means that the endophyte possesses genetic and/or metabolic characteristics that result in a beneficial phenotype in a plant harbouring, or otherwise associated with, the endophyte. Such beneficial properties include improved resistance to pests and/or diseases, improved tolerance to water and/or nutrient stress, enhanced biotic stress tolerance, enhanced drought tolerance, enhanced water use efficiency, reduced toxicity and enhanced vigour in the plant with which the endophyte is associated, relative to an organism not harboring the endophyte or harboring a control endophyte such as standard toxic (ST) endophyte.

The pests and/or diseases may include, but are not limited to, bacterial and/or fungal pathogens, preferably fungal. In a particularly preferred embodiment, the endophyte may result in the production of the bioprotectant compound in the plant with which it is associated.

As used herein, the term 'bioprotectant compound' is meant as a compound that provides or aids bioprotection to the plant with which it is associated against pests and/or diseases, such as bacterial and/or fungal pathogens. A bioprotectant compound may also be known as a 'biocidal compound'.

In a particularly preferred embodiment, the endophyte produces a bioprotectant compound and provides bioprotection to the plant against bacterial and/or fungal pathogens. The terms bioprotectant, bioprotective and bioprotection (or any other variations) may be used interchangeably herein.

Thus, in a preferred embodiment, the present invention provides a method of providing bioprotection to a plant against bacterial and/or fungal pathogens, said method including infecting the plant with an endophyte as hereinbefore described and cultivating the plant.

In a particularly preferred embodiment the bioprotectant compound is poaeamide or derivative, isomer and/or salt thereof.

The endophyte may be suitable as a biofertilizer to improve the availability of nutrients to the plant with which the endophyte is associated, including but not limited to improved tolerance to nutrient stress.

Thus, in a preferred embodiment, the present invention provides a method of providing biofertilizer to a plant, said method including infecting the plant with an endophyte as hereinbefore described and cultivating the plant.

The nutrient stress may be lack of or low amounts of a nutrient such as phosphate and/or nitrogen. The endophyte may be capable of growing in conditions such as low nitrogen and/or low phosphate and enable these nutrients to be available to the plant with which the endophyte is associated.

The endophyte may result in the production of organic acids and/or the solubilisation of phosphate in the plant with which it is associated and/or provide a source of phosphate to the plant.

Alternatively, or in addition, the endophyte may be capable of nitrogen fixation. Thus, if an endophyte is capable of nitrogen fixation, the plant with which the endophyte is associated may be capable of growing in low nitrogen conditions and/or the endophyte may provide a source of nitrogen to the plant.

In a particularly preferred embodiment, the endophyte provides the ability of the organism to grow in low nitrogen.

As used herein the term "plant of the Poaceae family" is a grass species, particularly a pasture grass such as ryegrass (*Lolium*) or fescue (*Festuca*), more particularly perennial ryegrass (*Lolium perenne* L.) or tall fescue (*Festuca arundinaceum*, otherwise known as *Lolium arundinaceum*).

In another aspect, the present invention provides a plant or part thereof infected with an endophyte as hereinbefore described. In preferred embodiments, the plant or part thereof infected with the endophyte may produce a bioprotectant compound, preferably poaeamide or derivative, isomer and/or salt thereof.

Also in preferred embodiments, the plant or part thereof includes an endophyte-free host plant or part thereof stably infected with said endophyte.

The plant inoculated with the endophyte may be a grass or non-grass plant suitable for agriculture, specifically a forage, turf, or bioenergy grass, or a grain crop or industrial crop.

Preferably, the plant is a grass species plant, specifically a forage, turf, bioenergy, grain crop or industrial crop grass.

The forage, turf or bioenergy grass may be those belonging to the *Brachiaria-Urochloa* species complex (panic grasses), including *Brachiaria brizantha, Brachiaria decumbens, Brachiaria humidicola, Brachiaria stolonifera, Brachiaria ruziziensis, B. dictyoneura, Urochloa brizantha, Urochloa decumbens, Urochloa humidicola, Urochloa mosambicensis* as well as interspecific and intraspecific hybrids of *Brachiaria-Urochloa* species complex such as interspecific hybrids between *Brachiaria ruziziensis* x *Brachiaria brizantha, Brachiaria ruziziensis* x *Brachiaria decumbens*, [*Brachiaria ruziziensis* x *Brachiaria decumbens*]x *Brachiaria brizantha*, [*Brachiaria ruziziensis* x *Brachiaria brizantha*]x *Brachiaria decumbens*.

The forage, turf or bioenergy grass may also be those belonging to the genera *Lolium* and *Festuca*, including *L. perenne* (perennial ryegrass) and *L. arundinaceum* (tall fescue) and *L. multiflorum* (Italian ryegrass).

The grain crop or industrial crop may be a non-grass species, for example, any of soybeans, cotton and grain legumes, such as lentils, field peas, fava beans, lupins and chickpeas, as well as oilseed crops, such as canola.

Thus, the grain crop or industrial crop species may be selected from the group consisting of wheat, barley, oats, chickpeas, triticale, fava beans, lupins, field peas, canola, cereal rye, vetch, lentils, millet/*panicum*, safflower, linseed, sorghum, sunflower, maize, canola, mungbeans, soybeans, and cotton.

The grain crop or industrial crop may be a grass belonging to the genus *Triticum*, including *T. aestivum* (wheat), those belonging to the genus *Hordeum*, including *H. vulgare* (barley), those belonging to the genus *Avena*, including *A. sativa* (oats), those belonging to the genus *Zea*, including *Z. mays* (maize or corn), those belonging to the genus *Oryza*, including *O. sativa* (rice), those belonging to the genus *Saccharum* including *S. officinarum* (sugarcane), those belonging to the genus Sorghum including *S. bicolor* (sorghum), those belonging to the genus *Panicum*, including *P. virgatum* (switchgrass), and those belonging to the genera *Miscanthus, Paspalum, Pennisetum, Poa, Eragrostis* and *Agrostis*.

A plant or part thereof may be infected by a method selected from the group consisting of inoculation, breeding, crossing, hybridisation, transduction, transfection, transformation and/or gene targeting and combinations thereof.

Without wishing to be bound by theory, it is believed that the endophyte of the present invention may be transferred through seed from one plant generation to the next. The endophyte may then spread or locate to other tissues as the plant grows, i.e. to roots. Alternatively, or in addition, the endophyte may be recruited to the plant root, e.g. from soil, and spread or locate to other tissues.

Thus, in a further aspect, the present invention provides a plant, plant seed or other plant part derived from a plant or part thereof as hereinbefore described. In preferred embodiments, the plant, plant seed or other plant part may produce a bioprotectant compound, preferably a poaeamide, or derivative, isomer and/or salt thereof.

In another aspect, the present invention provides the use of an endophyte as hereinbefore described to produce a plant or part thereof stably infected with said endophyte. The present invention also provides the use of an endophyte as hereinbefore described to produce a plant or part thereof as hereinbefore described.

In another aspect, the present invention provides a bioprotectant compound, preferably poaeamide, produced by an endophyte as hereinbefore described, or a derivative, isomer and/or a salt thereof.

The bioprotectant compound, preferably poaeamide, may be produced by the endophyte when associated with a plant, e.g. a plant of the Poaceae family as described above.

Thus, in another aspect, the present invention provides a method for producing a bioprotectant compound, preferably poaeamide, or a derivative, isomer and/or a salt thereof, said method including infecting a plant with an endophyte as hereinbefore described and cultivating the plant under conditions suitable to produce the bioprotectant compound, preferably poaeamide, or a derivative, isomer and/or a salt thereof.

The endophyte-infected plant or part thereof may be cultivated by known techniques. The person skilled in the art may readily determine appropriate conditions depending on the plant or part thereof to be cultivated.

The bioprotectant compound, preferably poaeamide, or a derivative, isomer and/or a salt thereof, may also be produced by the endophyte when it is not associated with a plant. Thus, in yet another aspect, the present invention provides a method for producing a bioprotectant compound, preferably poaeamide, or a derivative, isomer and/or a salt thereof, said method including culturing an endophyte as hereinbefore described, under conditions suitable to produce the bioprotectant compound.

The conditions suitable to produce the bioprotectant compound, preferably poaeamide, or a derivative, isomer and/or a salt thereof, may include a culture medium including a source of carbohydrates. The source of carbohydrates may be a starch/sugar-based agar or broth such as potato dextrose agar, potato dextrose broth or half potato dextrose agar or a cereal-based agar or broth such as oatmeal agar or oatmeal broth. Other sources of carbohydrates may include endophyte agar, Murashige and Skoog with 20% sucrose, half V8 juice/half PDA, water agar and yeast malt extract agar. The endophyte may be cultured under aerobic or anaerobic conditions and may be cultured in a bioreactor.

In a preferred embodiment of this aspect of the invention, the method may include the further step of isolating the bioprotectant compound, preferably poaeamide, or a derivative, isomer and/or a salt thereof, from the plant or culture medium.

The endophyte-infected plant or part thereof may be cultivated by known techniques. The person skilled in the art may readily determine appropriate conditions depending on the plant or part thereof to be cultivated.

The endophyte of the present invention may display the ability to solubilise phosphate.

Thus, in yet another aspect, the present invention provides a method of increasing phosphate use efficiency and/or increasing phosphate solubilisation by a plant, said method including infecting a plant with an endophyte as hereinbefore described, and cultivating the plant.

In yet another aspect, the present invention provides a method of reducing phosphate levels in soil, said method including infecting a plant with an endophyte as hereinbefore described, and cultivating the plant in the soil.

The endophyte of the present invention may be capable of nitrogen fixation. Thus, in yet another aspect, the present invention provides a method of growing the plant in low nitrogen containing medium, said method including infecting a plant with an endophyte as hereinbefore described, and cultivating the plant. Preferably, the low nitrogen medium is low nitrogen containing soil.

In yet a further aspect, the present invention provides a method of increasing nitrogen use efficiency or increasing nitrogen availability to a plant, said method including infecting a plant with an endophyte as hereinbefore described, and cultivating the plant.

In yet another aspect, the present invention provides a method of reducing nitrogen levels in soil, said method including infecting a plant with an endophyte as hereinbefore described, and cultivating the plant in the soil.

In a further aspect, the present invention provides a method of providing bioprotection to a plant against bacterial and/or fungal pathogens and/or providing biofertilizer to a plant, said method including infecting the plant with and endophyte as hereinbefore described. Preferably, the method includes providing bioprotection to the plant and includes production of a bioprotectant compound in the plant into which the endophyte is inoculated.

The endophyte-infected plant or part thereof may be cultivated by known techniques. The person skilled in the art may readily determine appropriate conditions depending on the plant or part thereof to be cultivated.

The production of a bioprotectant compound has particular utility in agricultural plant species, in particular, forage, turf, or bioenergy grass species, or grain crop species or industrial crop species. These plants may be cultivated across large areas of e.g. soil where the properties and biological processes of the endophyte as hereinbefore described and/or bioprotectant compound produced by the endophyte may be exploited at scale.

The part thereof of the plant may be, for example, a seed.

In preferred embodiments, the plant is cultivated in the presence of soil phosphate and/or nitrogen, alternatively or in addition to applied phosphate and/or nitrogen. The applied phosphate and/or applied nitrogen may be by way of, for example, fertiliser. Thus, preferably, the plant is cultivated in soil.

In preferred embodiments, the endophyte may be a *Pseudomonas poae* strain EY as described herein and as deposited with The National Measurement Institute of 1/153 Bertie Street, Port Melbourne, VIC 3207, Australia on 17 May 2019 with accession number V19/009907.

Preferably, the plant is a forage, turf, bioenergy grass species or, grain crop or industrial crop species, as hereinbefore described.

The part thereof of the plant may be, for example, a seed.

In preferred embodiments, the plant is cultivated in the presence of soil phosphate and/or applied phosphate. The applied phosphate may be by way of, for example, fertiliser. Thus, preferably, the plant is cultivated in soil.

Alternatively, or in addition, the plant is cultivated in the presence of soil nitrogen and/or applied nitrogen. The applied nitrogen may be by way of, for example, fertiliser. Thus, preferably, the plant is cultivated in soil.

The present invention will now be more fully described with reference to the accompanying Examples and drawings. It should be understood, however, that the description following is illustrative only and should not be taken in any way as a restriction on the generality of the invention described above.

BRIEF DESCRIPTION OF THE DRAWINGS/FIGURES

FIGS. 1—16S Amplicon sequence of novel bacterial strain EY (SEQ ID NO 1).

FIG. 2—Phylogeny of *Pseudomonas* spp. and novel bacterial strain EY. This maximum-likelihood tree was inferred based on 21 genes conserved among 19 genomes. Values shown next to branches were the local support values calculated using 1000 resamples with the Shimodaira-Hasegawa test.

Figure 3:
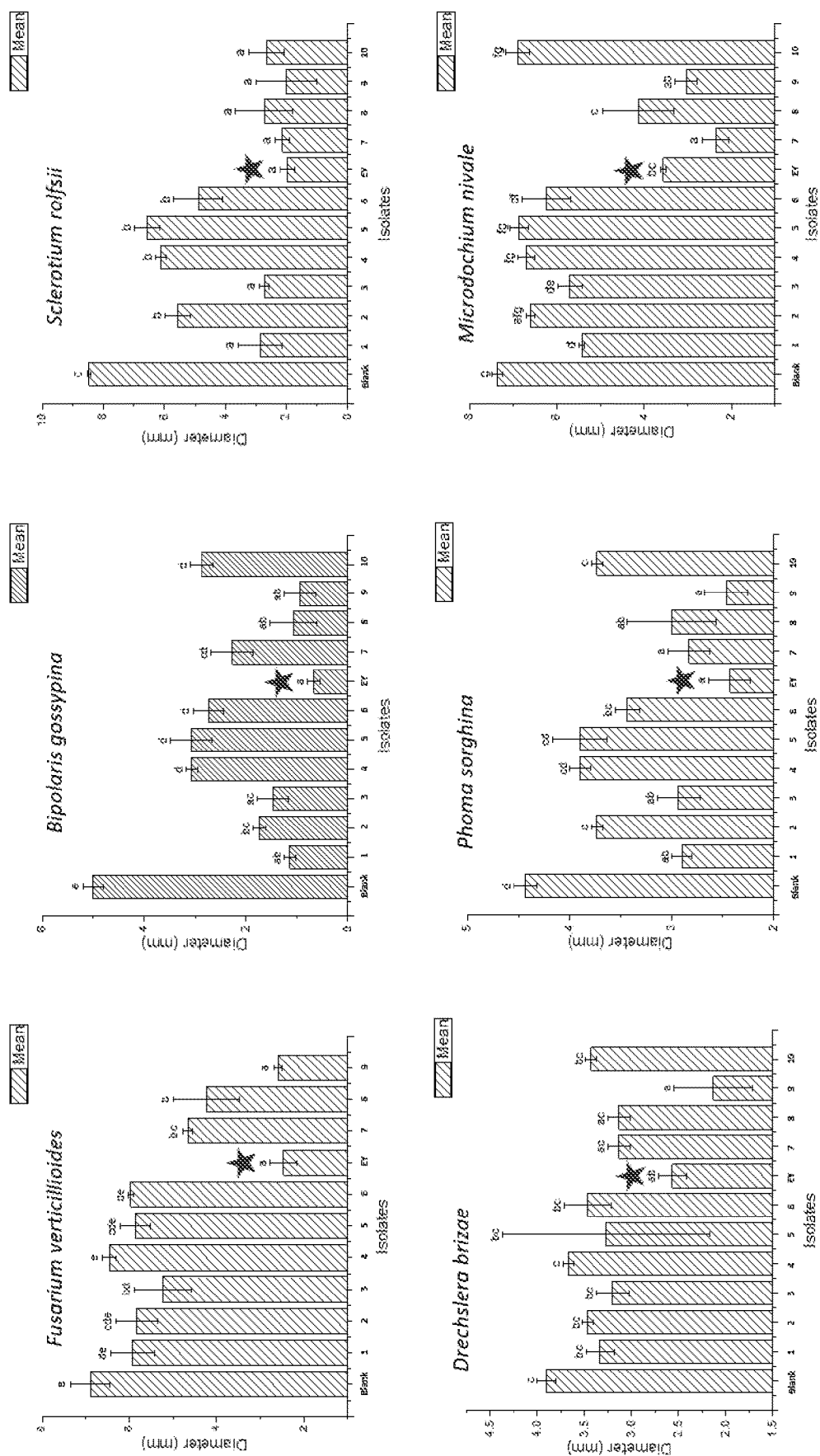

FIG. 3—Bioprotection bioassay indicating the growth of 11 strains (including *Pseudomonas poae* novel bacterial strain EY, star) against 6 plant pathogenic fungi, *Fusarium verticillioides* (10 days post inoculation, dpi), *Bipolaris gossypina* (7 dpi), *Sclerotinia rolfsii* (5 dpi), *Drechslera brizae* (8 dpi), *Phoma sorghina* (9 dpi) and *Microdochium nivale* (6 dpi). Bars represent the mean diameter of fungal colonies from three replicate plates of each treatment. Different superscript letters indicate significant differences ($P<0.05$) between treatments.

FIG. 4—Secondary metabolite biosynthesis gene clusters in *Pseudomonas poae* novel bacterial strain EY identified using antiSMASH (Weber et al. 2015). The gene clusters have sequence homology and structure to (A) the poaA gene cluster and (B) the poaB and poaC gene cluster. An additional 4 genes are present in the poaA gene cluster in strain EY, including an ABC transporter binding protein (i), ABC transporter permease (ii), cyclodehydratase (iii) and an oxidoreductase (iv) that are all involved in microcin biosynthesis.

Figure 5:
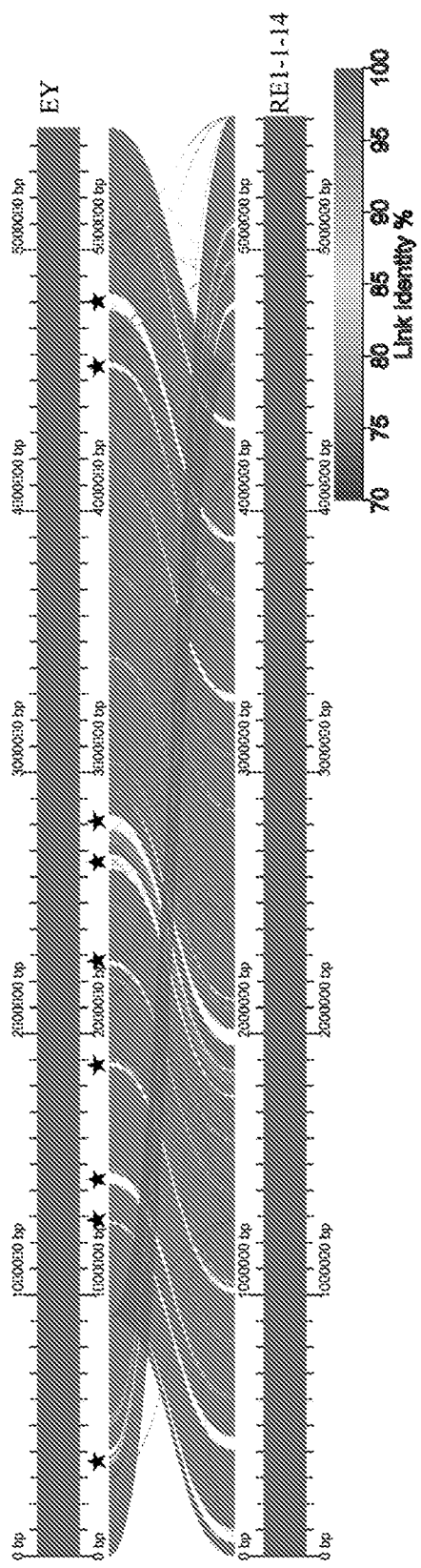

FIG. 5—Whole genome sequence comparison of *Pseudomonas poae* novel bacterial strain EY (top) and *Pseudomonas poae* bacterial strain RE1-1-14 (bottom). The links between genome sequences indicated percentage similarity (from 70% to 100%). Genetic variations, including non-identical regions and insertions/deletions/inversions, suggest that *Pseudomonas poae* bacterial strains EY and RE1-1-14 are genetically different. Stars represent genomic regions unique to *Pseudomonas poae* bacterial strains EY (dark grey stars) or RE1-1-14 (light grey stars).

Figure 6:
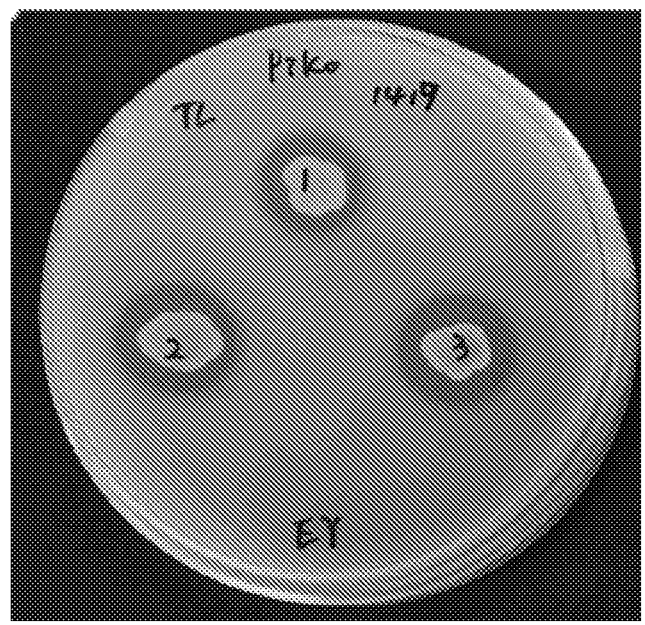

FIG. 6—Biofertiliser activity (in vitro) of the *Pseudomonas poae* novel bacterial strain EY on Pikovskaya's Agar, which determines the ability of bacteria to solubilise inorganic phosphate.

Figure 7:
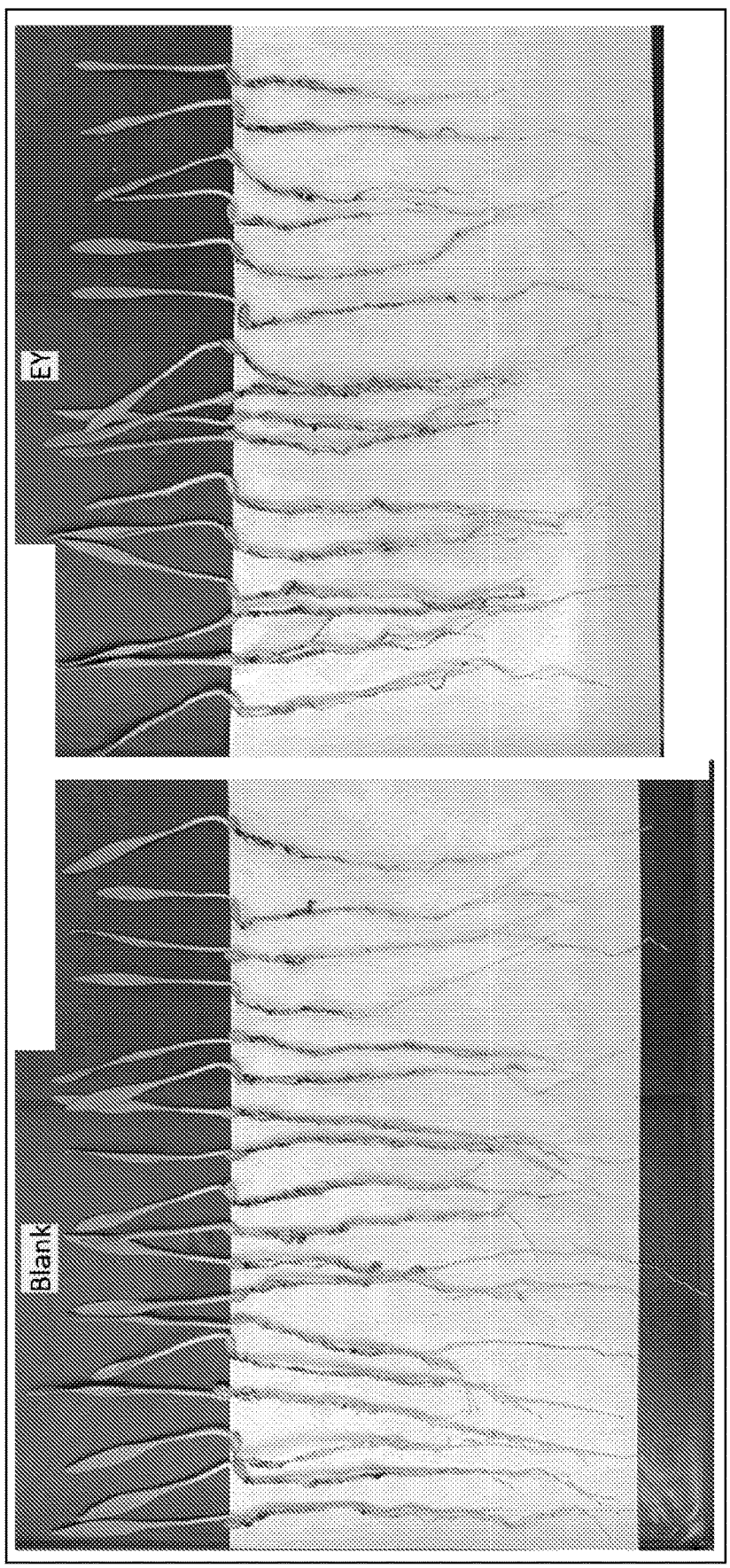

FIG. 7—Image of 5 day old seedlings (11) inoculated with the *Pseudomonas poae* novel bacterial strain EY and an untreated control.

Figure 8:
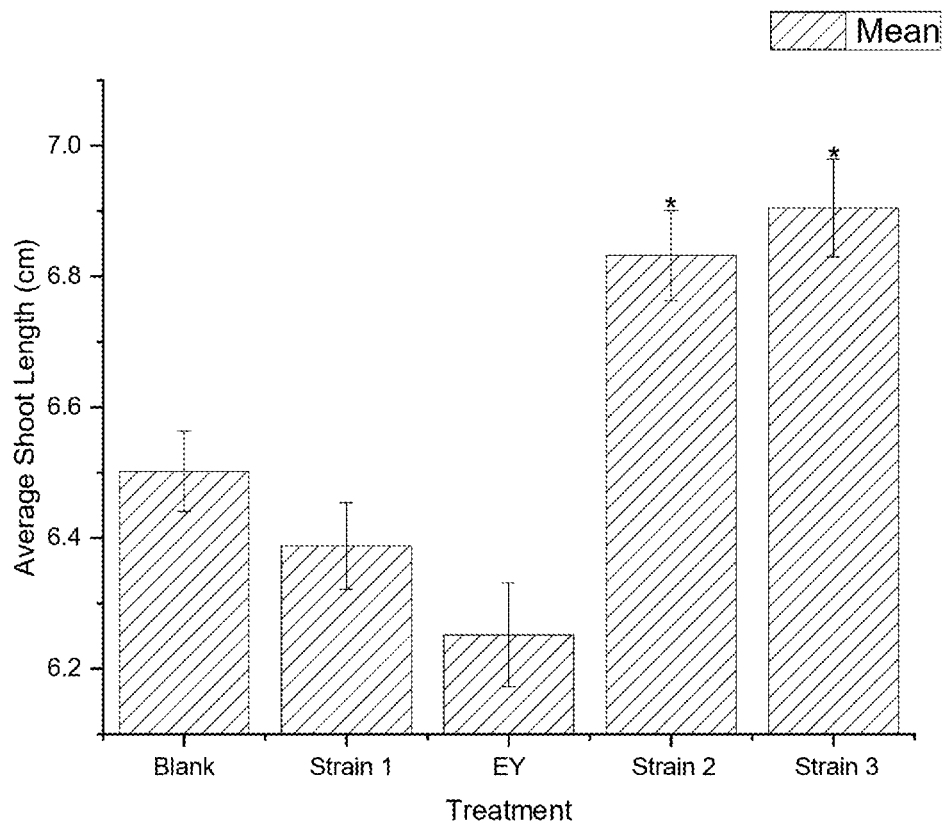

FIG. 8—Average shoot length of barley seedlings inoculated with bacterial strains of Pseudomonas poae (novel strain EY) and non-Pseudomonads (Strain 1, 2, 3), and grown for 5 days. The * indicates significant difference in the mean at p 0.05 between the control and the bacterial strains.

Figure 9:
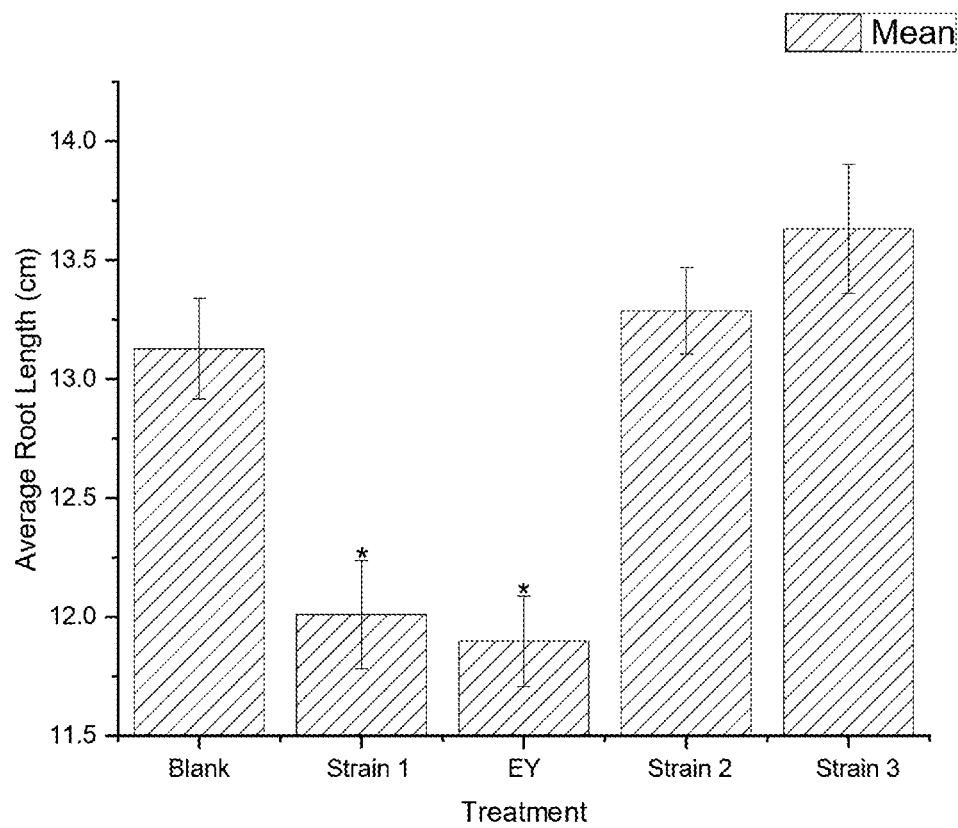

FIG. 9—Average root length of barley seedlings inoculated with bacterial strains of Pseudomonas poae (novel strain EY) and non-Pseudomonads (Strain 1, 2, 3), and grown for 5 days. The * indicates significant difference in the mean at p 0.05 between the control and the bacterial strains.

Figure 10:
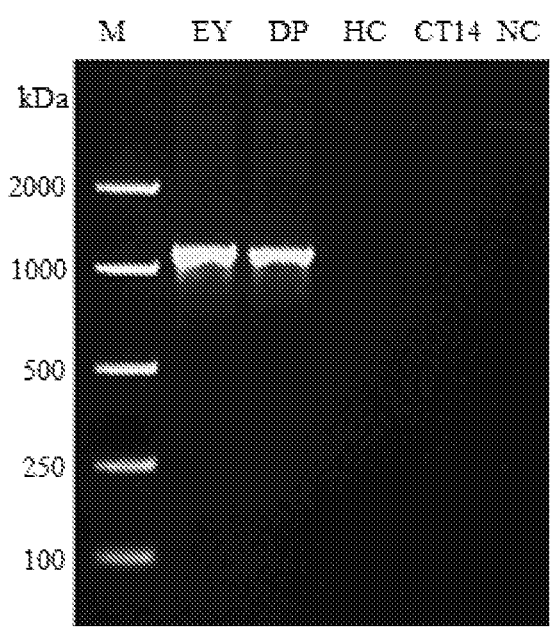

FIG. 10—Agarose gel electrophoresis (2% [w/v]) of PCR amplicons generated using the EY strain-specific primers on Pseudomonas poae bacterial strain EY, closely related strains (DP, HC, CT14) a negative control (NC) and a 2 kb DNA molecular ladder (M)

Figure 11:
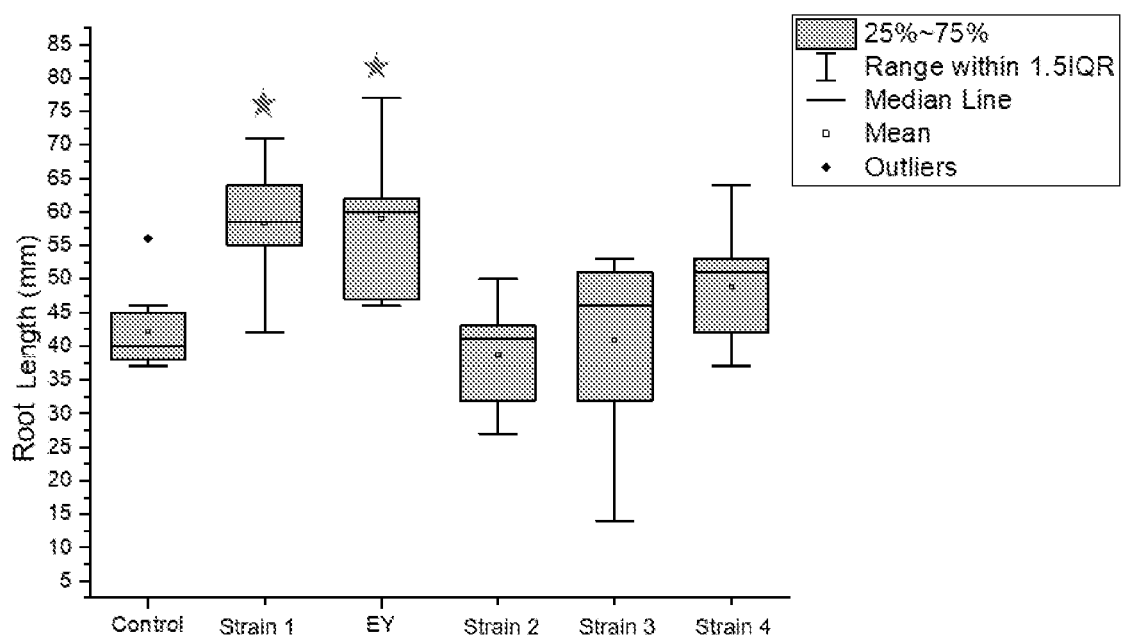

FIG. 11—Average root length of barley seedlings inoculated with bacterial strains of Pseudomonas poae. (strain EY) and non-Pseudomonads (Strain 1, 2, 3, 4), and grown for 4 days on nitrogen free media. The star indicates significant difference in the mean at p 0.05 between the control and the bacterial strains.

Figure 12:
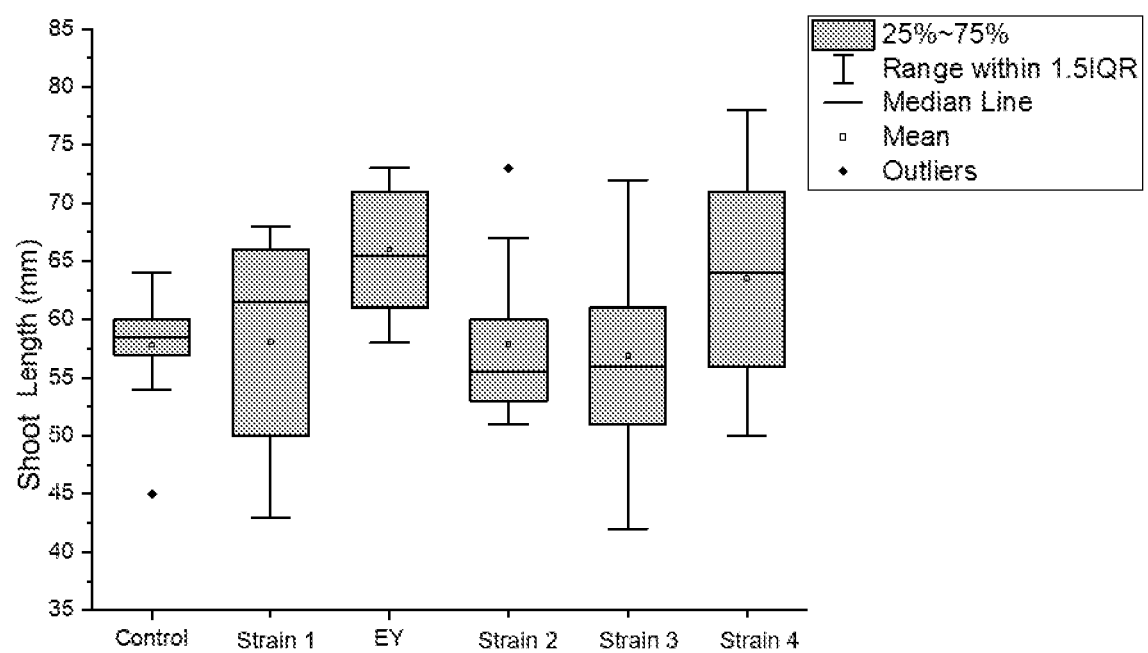

FIG. 12—Average shoot length of barley seedlings inoculated with bacterial strains of Pseudomonas poae. (strain EY) and non-Pseudomonads (Strain 1, 2, 3, 4), and grown for 4 days on nitrogen free media. The star indicates significant difference in the mean at p 0.05 between the control and the bacterial strains.

Figure 13:
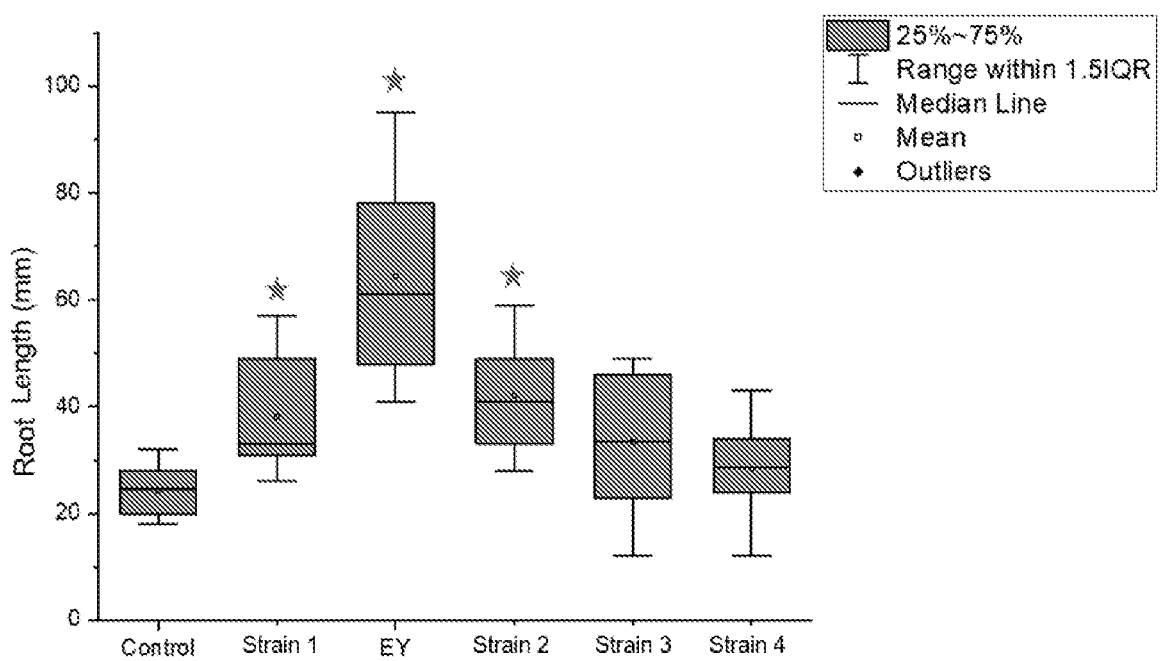

FIG. 13—Average root length of barley seedlings inoculated with bacterial strains of Pseudomonas poae. (strain EY) and non-Pseudomonads (Strain 1, 2, 3, 4) and grown for 4 days on media containing insoluble phosphate. The star indicates significant difference in the mean at p 0.05 between the control and the bacterial strains.

Figure 14:
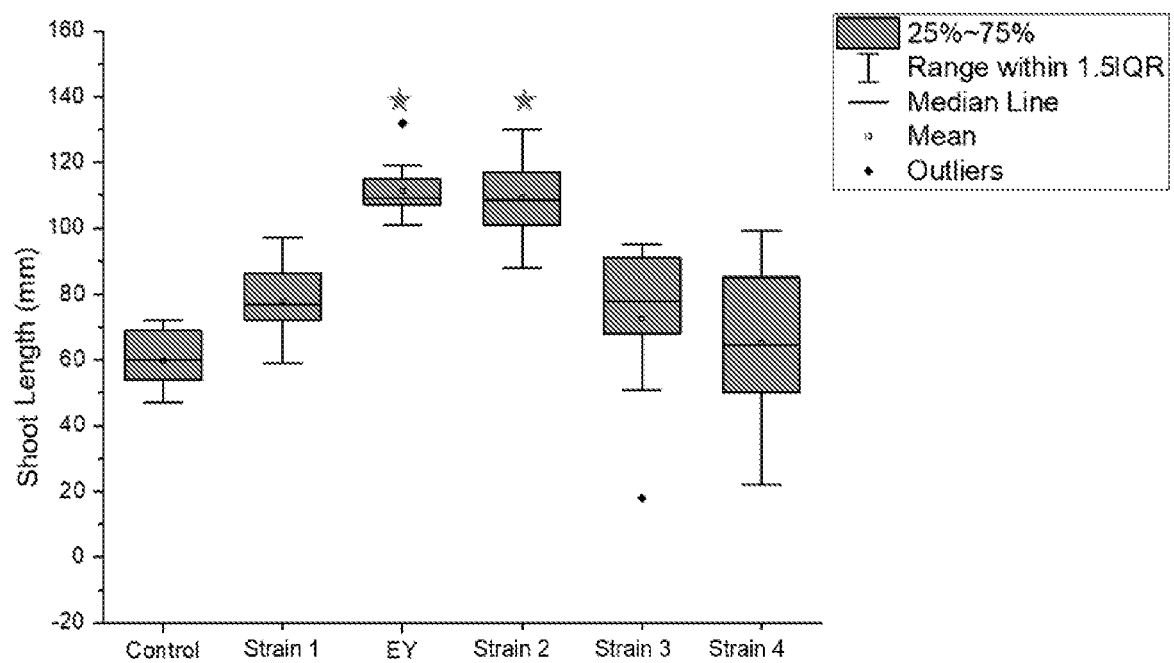

FIG. 14—Average shoot length of barley seedlings inoculated with bacterial strains of Pseudomonas poae. (strain EY) and non-Pseudomonads (Strain 1, 2, 3, 4) and grown for 4 days on media containing insoluble phosphate. The star indicates significant difference in the mean at p 0.05 between the control and the bacterial strains.

Figure 15:
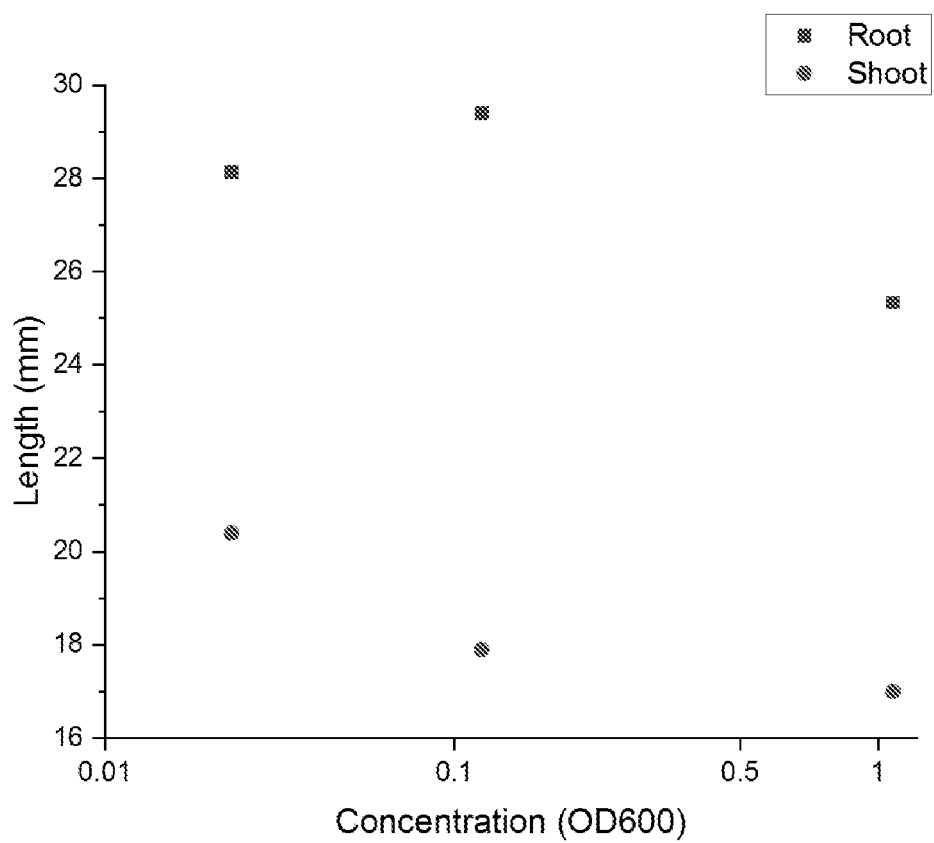

FIG. 15—Average root and shoot length of barley seedlings inoculated with novel Pseudomonas poae bacterial strain EY at different concentrations ($10^0$, $10^{-1}$, $10^{-2}$), and grown for 7 days.

DETAILED DESCRIPTION OF THE EMBODIMENTS

Isolation and Characterisation of Plant Associated Pseudomonas poae Novel Bacterial Strains Providing Bioprotection and Biofertilizer Phenotypes to Plants.

The novel plant associated Pseudomonas poae bacterial strain EY has been isolated from perennial ryegrass (Lolium perenne) plants. It displays the ability to inhibit the growth of plant fungal pathogens and solubilise phosphate in plate assays. The genome of the Pseudomonas poae bacterial strain EY has been sequenced and is shown to be novel, related to bioprotectant Pseudomonas poae strains and not pathogenic Pseudomonad bacteria. Analysis of the genome sequence has shown that the Pseudomonas poae novel bacterial strain EY has gene clusters for the biosynthesis of the bioprotectant compound poaeamide, genes involved in biofertilisation via the production of organic acids and the solubilisation of phosphate, while there is an absence of virulence-related genes (effectors) suggesting the strain has an endophytic life cycle. This novel bacterial strain has been used to inoculate barley (Hordeum vulgare) seeds under glasshouse conditions and has been demonstrated not to cause disease in these barley plants. These barley plants are also able to produce seed. Novel bacterial strain EY also enhances root and shoot growth in nitrogen limiting conditions and in insoluble phosphate. The optimal concentration of inoculum for novel bacterial strain EY is a dilution of an overnight culture ($10^{-1}$, $10^{-2}$). Overall, novel plant associated Pseudomonas poae bacterial strain EY offer both bioprotectant and biofertilizer activity.

Example 1—Isolation of Bacterial Strains

Seed Associated Bacterial Strains

Seeds from perennial ryegrass (Lolium perenne) were surface-sterilised by soaking in 80% ethanol for 3 mins, then washing 5 times in sterile distilled water. The seeds were then plated onto sterile filter paper soaked in sterile water in sterile petri dishes. These plates were stored at room temperature in the dark to allow seedlings to germinate for 1-2 weeks. Once the seedlings were of sufficient size, the plants were harvested. In harvesting, the remaining seed coat was discarded, and the aerial tissue and root tissue were harvested. The plant tissues were submerged in sufficient Phosphate Buffered Saline (PBS) to completely cover the tissue, and ground using a Qiagen TissueLyser II, for 1 minute at 30 Hertz. A 10 µl aliquot of the macerate was added to 90 µl of PBS. Subsequent 1 in 10 dilutions of the $10^{-1}$ suspension were used to create additional $10^{-2}$ to $10^{-4}$ suspensions. Once the suspensions were well mixed 50 µl aliquots of each suspension were plated onto Reasoners 2 Agar (R2A) for growth of bacteria. Dilutions that provided a good separation of bacterial colonies were subsequently used for isolation of individual bacterial colonies through re-streaking of single bacterial colonies from the dilution plates onto single R2A plates to establish a pure bacterial colony.

Mature Plant Associated Bacterial Strains

Leaf and root tissue were harvested from mature plants grown in the field or grown in pots in a greenhouse. Root tissue was washed in PBS buffer to remove soil particles and sonicated (10 mins) to remove the rhizosphere. The harvested tissues were placed into sufficient PBS to completely cover the tissue and processed as per the previous section to isolate pure bacterial cultures.

Around 300 bacterial strains were obtained from sterile seedlings, and 300 strains from mature plants. The novel bacterial strain EY was collected from seed of perennial ryegrass.

Example 2—Identification of Pseudomonas poae Novel Bacterial Strain

Amplicon (16S rRNA Gene) Sequencing

A phylogenetic analysis of the novel bacterial strain EY was undertaken by sequence homology comparison of the 16S rRNA gene. The novel bacterial strain EY was grown overnight in Reasoners 2 Broth (R2B) media. DNA was extracted from pellets derived from the overnight culture using a DNeasy Blood and Tissue kit (Qiagen) according to manufacturer's instructions. The 16S rRNA gene amplification used the following PCR reagents: 14.8 µL $H_2O$, 2.5 µL 10×reaction buffer, 0.5 µL 10 mM dNTPs, 2.5 µL each of the 5 µM 27F primer (5'-AGAGTTTGATCMTGGCTCAG-3') (SEQ ID NO. 2) and 5 µM reverse primers 1492R (5'-GGTTACCTTGTTACGACTT-3') (SEQ ID NO 3), 0.2 µL of Immolase enzyme, and template to a final volume of 25 µL. The PCR reaction was then run in an Agilent Surecylcer 8800 (Applied Biosystems) with the following program; a denaturation step at 94° C. for 15 min; 35 cycles of 94° C. for 30 sec, 55° C. for 10 sec, 72° C. 1 min; and a final extension step at 72° C. for 10 min.

Shrimp alkaline phosphatase (SAP) exonuclease was used to purify the 16S rRNA gene PCR amplicon. The SAP amplicon purification used the following reagents: 7.375 μL $H_2O$, 2.5 μL 10×SAP, and 0.125 μL Exonuclease I. The purification reaction was incubated at 37° C. for 1 hr, followed by 15 min at 80° C. to deactivate the exonuclease.

The purified 16S rRNA gene amplicon was sequenced using the BigDye® Terminator v3.1 Cycle Sequencing Kit (Thermofisher) with the following reagents; 10.5 μL $H_2O$, 3.5 μL 5×Seq buffer, 0.5 μL BigDye®, 2.5 μL of either the 3.2 μM Forward (27F) and 3.2 μM Reverse primers (1492R), and 4.5 μL of PCR amplicon as template, to a final reaction volume of 20 μL. The sequencing PCR reaction was then run in an Agilent Surecylcer 8800 (Applied Biosystems) with the following program; denaturation step at 94° C. for 15 min; followed by 35 cycles of 94° C. for 30 sec, 55° C. for 10 sec, 72° C. 1 min; and one final extension step at 72° C. for 10 min. The 16S rRNA gene amplicon from novel bacterial strain EY was sequenced on an ABI3730XL (Applied Biosystems). A 1278 bp 16S rRNA gene sequence was generated (FIG. 1). The sequence was aligned by BLASTn on NCBI against the non-redundant nucleotide database and the 16S ribosomal RNA database.

BLASTn Hit Against Database Nr
*Pseudomonas poae* Strain HTM601-1 16S Ribosomal RNA Gene, Partial Sequence

| Max Score | Total Score | Query Coverage | E-Value | % Identity | Accession |
|---|---|---|---|---|---|
| 2361 | 2361 | 100% | 0 | 100.00% | MG835948.1 |

BLASTn Hit Against Database 16S Ribosomal RNA
*Pseudomonas poae* Strain P 527/13 16S Ribosomal RNA Gene, Partial Sequence

| Max Score | Total Score | Query Coverage | E-Value | % Identity | Accession |
|---|---|---|---|---|---|
| 2355 | 2355 | 100% | 0 | 99.92% | NR_028986.1 |

The preliminary taxonomic identification of the novel bacterial strain EY was *Pseudomonas poae*.

Genomics

The genome of novel bacterial strain EY was sequenced. This novel bacterial strain was retrieved from the glycerol collection stored at −80° C. by streaking on R2A plates. Single colonies from these plates were grown overnight in Nutrient Broth and pelleted. These pellets were used for genomic DNA extraction using the bacteria protocol of Wizard® Genomic DNA Purification Kit (A1120, Promega). A DNA sequencing library was generated for Illumina sequencing using the Illumina Nextera XT DNA library prep protocol. The library was sequenced using an Illumina MiSeq platform or HiSeq platform. Raw reads from the sequencer were filtered to remove any adapter and index sequences as well as low quality bases using Trimmomatic (Bolger, Lohse & Usadel 2014) with the following options: ILLUMINACLIP: NexteraPE-PE.fa:2:30:10 LEADING:3 TRAILING:3 SLIDINGWINDOW:4:15 MINLEN:36. To enable full genome assembly, long reads were generated for novel bacterial strain EY only by sequencing DNA using Oxford Nanopore Technologies (ONT) MinION platform. The DNA from the Wizard® Genomic DNA Purification Kit was first assessed with the genomic assay on Agilent 2200 TapeStation system (Agilent Technologies, Santa Clara, CA, USA) for integrity (average molecular weight 30 Kb). The sequencing library was prepared using an in-house protocol modified from the official protocols for transposases-based library preparation kits (SQK-RAD004/SQK-RBK004, ONT, Oxford, UK). The library was sequenced on a MinION Mk1B platform (MIN-101B) with R9.4 flow cells (FLO-MIN106) and under the control of MinKNOW software. After the sequencing run finished, the fast5 files that contain raw read signals were transferred to a separate, high performance computing Linux server for local basecalling using ONT's Albacore software (Version 2.3.1) with default parameters. The sequencing summary file produced by Albacore was processed by the R script minion_qc (https://github.com/roblanf/minion_qc) and NanoPlot (De Coster et al. 2018) to assess the quality of the sequencing run, while Porechop (Version 0.2.3, https://github.com/rrwick/Porechop) was used to remove adapter sequences from the reads. Reads which were shorter than 300 bp were removed and the worst 5% of reads (based on quality) were discarded by using Filtlong (Version 0.2.0, https://github.com/rrwick/Filtlong).

The whole genome sequence of novel bacterial strain EY was assembled using Unicycler (Wick et al. 2017). Unicycler performed hybrid assembly when both Illumina reads and MinION reads were available. MinION reads were mainly used to resolve repeat regions in the genome, whereas Illumina reads were used by Pilon (Walker et al. 2014) to correct small base-level errors. Multiple rounds of Racon (Vaser et al. 2017) polishing were then carried out to generate consensus sequences. Assembly graphs were visualised by using Bandage (Wick et al. 2015).

A complete circular chromosome sequence was produced for the novel bacterial strain EY. The genome size for the novel bacterial strain EY was 5,469,454 bp (Table 1). The percent GC content was 60.99%. The novel bacterial strain EY was annotated by Prokka (Seemann 2014) with a custom, genus-specific protein database to predict genes and corresponding functions, which were then screened manually to identify specific traits. The number of genes for the novel bacterial strain EY was 4,877 (Table 2).

TABLE 1

Summary of properties of the final genome sequence assembly

| Strain ID | Genome size (bp) | GC content (%) | Coverage Illumina reads | Coverage ONT MinION |
|---|---|---|---|---|
| EY | 5,469,454 | 60.99 | 115× | 40× |

TABLE 2

Summary of genome coding regions

| Strain ID | Genome size (bp) | No. of tRNA | No. of tmRNA | No. of rRNA | No. of CDS | No. of gene |
|---|---|---|---|---|---|---|
| EY | 5,469,454 | 69 | 1 | 16 | 4,791 | 4,877 |

Eighteen *Pseudomonas* spp. (*P. fluorescens, P. chlororaphis, P. syringae, P. putida, P. stutzeri, P. aeruginosa, P. oryzihabitans*) genome sequences that are publicly available on NCBI were acquired and used for pan-genome/comparative genome sequence analysis alongside the novel bacterial strain EY. A total of 21 genes that are shared by all 19 *Pseudomonas* spp. bacterial strains were identified by running Roary (Page et al. 2015). PRANK (Löytynoja 2014) was then used to perform a codon aware alignment. A maximum-likelihood phylogenetic tree (FIG. 4) was inferred using FastTree (Price, Dehal & Arkin 2010) with Jukes-Cantor Joins distances and Generalized Time-Reversible and CAT approximation model. Local support values for branches were calculated using 1000 resamples with the Shimodaira-Hasegawa test. The novel bacterial strain EY clustered tightly with the bioprotectant *Pseudomonas poae* bacterial strain RE1-1-14, suggesting a close phylogenetic relationship between these two bacterial strains. Moreover, this cluster was separated from other *Pseudomonas* spp. with strong local support value (100%). This separation supports that bacterial strain EY is novel and from the species *Pseudomonas poae*.

The average nucleotide identity (ANI) was calculated for novel bacterial strain EY against *Pseudomonas poae* bacterial strain RE1-1-14. The genome sequences were aligned and compared using minimap2 (Li 2018). The ANI between bacterial strains EY and RE1-1-14 was 99.46%. Based on a species boundary of 95-96% (Chun et al. 2018; Richter & Rossello-Mora 2009) bacterial strain EY is a novel strain of the species *Pseudomonas poae* (Müller et al. 2013).

A maximum-likelihood tree was inferred based on 21 genes conserved among 19 genomes (FIG. 2).

Example 3—Bioprotection Activity (In Vitro) of the *Pseudomonas poae* Novel Bacterial Strain EY In vitro bioassays were established to test the bioactivity of 11 plant associated bacterial strains including *Pseudomonas poae* novel bacterial strain EY, against six plant pathogenic fungi (Table 3). A plate with only the pathogen was used as a negative control (blank). The fungal pathogens were all isolated from monocot species, and were obtained from the National Collection of Fungi (Herbarium VPRI) and the AVR collection. Each bacterial strain was cultured in Nutrient Broth (BD Biosciences) overnight at 28° C. in a shaking incubator (200 rpm). Each bacterial strain was drop-inoculated (20 µL) onto four equidistant points on a Nutrient Agar (BD Biosciences) plate, which was then incubated overnight at 28° C. A 6 mm×6 mm agar plug of actively growing mycelia from the pathogen was placed at the centre of the plate. The bioassay was incubated for at least 5 days at 28° C. in the dark, and then the diameter of the fungal colony on the plate was recorded. For each treatment three plates were prepared as biological triplicates. OriginPro 2018 (Version b9.5.1.195) was used to carry out One-way ANOVA and Tukey Test to detect the presence of any significant difference (p≤0.05) between treatments.

TABLE 3

Pathogens used in the bioprotection bioassay.

| VPRI Accession No. | Taxonomic Details | Host Taxonomic Details | State | Collection Date |
|---|---|---|---|---|
| 12962 | *Drechslera brizae* (Y. Nisik.) Subram. & B. L. Jain | *Briza maxima* L. | Vic. | 24 Oct. 85 |
| 32148 | *Sclerotium rolfsii* Sacc. | *Poa annua* L. | Vic. | 1 Jan. 5 |

TABLE 3-continued

Pathogens used in the bioprotection bioassay.

| VPRI Accession No. | Taxonomic Details | Host Taxonomic Details | State | Collection Date |
|---|---|---|---|---|
| 10694 | *Phoma sorghina* (Sacc.) Boerema, Dorenbosch, van Kesteren | *Cynodon dactylon* Pers. | Vic. | 19 Apr. 79 |
| 42586a | *Fusarium verticillioides* (Sacc.) Nirenberg | *Zea mays* L. | Vic. | 27 Feb. 15 |
| 42563 | *Bipolaris gossypina* | *Brachiaria* | Qld | |
| N/A | *Microdochium nivale* | *Lolium perenne* L. | Vic | |

The *Pseudomonas poae* novel bacterial strain EY inhibited the growth of all six fungal pathogens compared to the control and many of the other test bacterial strains, indicating it had broad spectrum biocidal activity (FIG. 3). The *Pseudomonas poae* novel bacterial strain EY was the most active bacterial strain against *Fusarium verticillioides, Bipolaris gossypina, Sclerotium rolfsii* and *Phoma sorghina*, while it was the second most active strain against *Drechslera brizae* and *Microdochium nivale*.

Example 4—Genome Sequence Features Supporting the Bioprotection Niche of the *Pseudomonas poae* Novel Bacterial Strain EY Secondary Metabolite Biosynthesis Gene Clusters The genome sequence of *Pseudomonas poae* novel bacterial strain EY was assessed for the presence of features associated with bioprotection. The annotated genome was analysed by antiSMASH (Weber et al. 2015) to identify secondary metabolite biosynthesis gene clusters that are commonly associated with the production of biocidal compounds that aid in their defence. An annotated genome was passed through antiSMASH with the following options: --clusterblast--asf--knownclusterblast--subclusterblast--smcogs--full-hmmer. A total of two secondary metabolite gene clusters were identified in the genome sequence of the *Pseudomonas poae* novel bacterial strain EY. (FIG. 4). The two biosynthetic gene clusters (cluster 1—poaA; cluster 2—poaB and poaC) had sequence homology (99%) and structure to the poeamide gene cluster that produces the bioprotectant non-ribosomal peptide poaeamide (FIG. 4). This gene cluster had the non-ribosomal peptide synthases (NRPS—poaA, poaB, poaC) essential for the biosynthesis of poaeamide and was similar in structure compared to the reference strain (RE1-1-14). In the poaA gene cluster of EY there is the presence of an additional four genes with sequence homology to genes involved in microcin biosynthesis, including an ABC transporter binding protein, ABC transporter permease, cyclodehydratase and an oxidoreductase (FIG. 4A). Some of these additional genes are likely to interact with poaeamide to alter the structure and produce a slightly different compound to poaeamide.

Genome Sequence Alignment

The genome sequences of *Pseudomonas poae* novel bacterial strain EY and the bioprotectant *Pseudomonas poae* strain RE1-1-14 were aligned using LASTZ (Version 1.04.00, http://www.bx.psu.edu/~rsharris/lastz/) and visualised using AliTV (Ankenbrand et al. 2017) to determine the genomic similarity between the two strains. The genome sequences of the two strains were similar, but there were large genomic regions unique to the novel bacterial strain EY (red stars) or the bacterial strain RE1-1-14 (yellow stars) (FIG. 5).

Example 5—Biofertiliser Activity (In Vitro) of the Pseudomonas poae Novel Bacterial Strain EY Phosphate is an essential ion for plant growth. Phosphate is applied to fields to improve plant growth and yield. A large amount of applied phosphate is not accessible to plants. Some bacteria have been shown to have the ability to mobilise some of this inaccessible phosphate. The P-solubilisation ability of bacterial strains was detected by using the Pikovskaya's Agar (Sundar ORacand & Sinha 1963), which contains inorganic phosphate in the form of calcium phosphate (5 g/L). *Pseudomonas poae* novel bacterial strain EY and *Escherichia coli* (negative control) were inoculated onto Pikovskaya's Agar at three equidistant points on a plate. All plates were then incubated for 72 hours at room temperature, and inspected visually for the formation of a clear zone around the colony. For each strain three plates were prepared as biological triplicates. The *Pseudomonas poae* novel bacterial strain EY was able to solubilise inorganic phosphate, as evidenced by a zone of clearing around the colony (FIG. 6).

Example 6—Genome Sequence Features Supporting the Biofertiliser Niche of the Pseudomonas poae Novel Bacterial Strain EY A number of bacterial and fungal species have been reported to solubilise inorganic phosphate. The mechanism of inorganic phosphate solubilization is via the production of mineral dissolving compounds such as organic acids (i.e. oxalic acid, citric acid, lactic acid, gluconic acid), siderophores, protons, hydroxyl ions and $CO_2$ (Rodriguez & Fraga 1999; Sharma, Kumar & Tripathi 2017). Organic acids together with their carboxyl and hydroxyl ions chelate cations or reduce the pH to release Phosphorous (Tallapragada & Seshachala 2012). A total of 4,877 genes in the annotated genome sequence of *Pseudomonas poae* novel bacterial strain EY were assessed for nomenclature consistent with the production of organic acids and the solubilisation of phosphate. Enzymes involved in organic acid production were identified including glucose dehydrogenases (gluconic acid), gluconate dehydrogenase (2-ketogluconic acid) and lactate dehydrogenase (lactic acid).

Example 7—Genome Sequence Features Supporting the Endophytic Niche of the Pseudomonas poae Novel Bacterial Strain EY There have been 57 virulence-related type III effector repertoires (genes) identified in *Pseudomonas syringae* pathovars that are important for the pathogenicity of this species (Lindeberg, Cunnac & Collmer 2012). These effectors are important for invading the host, suppressing the host immune system and altering host physiology for the benefit of the pathogen (Henry et al. 2017). A total of 50 type III effector repertoires were assessed for presence/absence in the genome sequence of novel bacterial strain EY (*Pseudomonas poae*), along with bacterial strains RE1-1-14 (*Pseudomonas poae*), B28a (*Pseudomonas syringae* pv. *syringae*), ICMP18708 (*Pseudomonas syringae* pv. *actinidae*) and PP1 (*Pseudomonas syringae* pv. *pisi*) through sequence homology searches (Blastp, 80% similarity, e-value 10-10) (Table 4). The *Pseudomonas poae* novel bacterial strain EY had only one of the 50 type III effector repertoires (HopJ). There was an absence of many of the key effectors involved in the pathogenicity of *Pseudomonas syringae*, including AVRE1 and Hop1 (Wei, Zhang & Collmer 2018).

TABLE 4

Fifty type III effector repertoires (genes) identified in *Pseudomonas syringae* pathovars and *Pseudomonas poae* strains (EY and RE1-1-14)

| | P. poae (EY) | P. poae (RE 1-1-14) | Pss (B728a) | Psa (ICMP 18708) | Psp (PP1) |
|---|---|---|---|---|---|
| avrB3 | | | | + | + |
| avrB4-1 | | | | | |
| avrE1 | | | + | + | + |
| avrPphB | | | | | |
| avrPto | | | | | |
| avrRpm1 | | | + | + | |
| avrRps4 | | | | | + |
| hopA1 | | | | + | |
| hopAA1 | | | + | | + |
| hopAA1-1 | | | | + | |
| hopAA1-2 | | | | + | |
| hopAB1 | | | + | | |
| hopAC1 | | | + | + | + |
| hopAE1 | | | + | | + |
| hopAF1 | | | + | | + |
| hopAG::ISPssy | | | | + | |
| hopAG1 | | | + | + | + |
| hopAH1 | | | + | + | + |
| hopAH2 | | | + | | + |
| hopAH2-1 | | | | + | |
| hopAH2-2 | | | | + | |
| hopAI1 | | | | + | |
| hopAJ1 | | | | | + |
| hopAJ2 | | | + | + | + |
| hopAK1 | | | + | + | + |
| hopAM1-1 | | | | + | + |
| hopAN1 | | | + | + | + |
| hopAO1 | | | | | |
| hopAS1 | | | | + | |
| hopAU1 | | | | + | |
| hopAV1 | | | | + | |
| hopAW1 | | | | + | |
| hopC1 | | | | | + |
| hopD1 | | | | + | |
| hopE1 | | | | | + |
| hopF2 | | | | | |
| hopH1 | | | + | + | + |
| hopI1 | | | + | + | + |
| hopJ1 | + | + | + | + | + |
| hopL1 | | | + | | + |
| hopM1 | | | + | | + |
| hopN1 | | | | + | |
| hopQ1-1 | | | | + | |
| hopR1 | | | | + | + |
| hopS2 | | | | + | |
| hopW1 | | | | + | |
| hopX1 | | | + | | + |
| hopY1 | | | | + | |
| hopZ3 | | | + | | |
| hrpK1 | | | + | | + |

Example 8—in Planta Inoculations Supporting Endophytic Niche of the Pseudomonas poae Novel Bacterial Strain EY To assess direct interactions between the *Pseudomonas poae* novel bacterial strain EY and plants, an early seedling growth assay was established in barley. A total of 4 bacterial strains (EY—*Pseudomonas poae*; Strain 1, Strain 2, Strain 3) were cultured in Lysogeny Broth (LB) overnight at 26° C. The following day seeds of barley (cultivar Hindmarsh)

were surface-sterilised by soaking in 80% ethanol for 3 mins, then washing 5 times in sterile distilled water. The seeds were then soaked in the overnight cultures for 4 hours at 26° C. in a shaking incubator. For control seedlings, seeds were soaked in LB without bacteria for 4 hours at 26° C. in a shaking incubator. The seeds were planted into a pot trial, with three replicates (pots) per strain/control, with a randomised design. A total of 20 seeds were planted per pot, to a depth of 1 cm. The potting medium contained a mixture of 25% potting mix, 37.5% vermiculite and 37.5% perlite. The plants were grown for 5 days and then removed from the pots, washed, assessed for health (i.e. no disease symptoms) and photographed. The lengths of the longest root and the longest shoot were measured. Data was statistically analysed using a one-way ANOVA and Tukey test to detect the presence of any significant difference ($p \leq 0.05$) between treatments using OriginPro 2018 (Version b9.5.1.195).

Seedlings inoculated with the *Pseudomonas poae* novel bacterial strain EY were healthy with no disease symptoms recorded on leaves or roots (FIG. 7). The length of the shoots inoculated with the *Pseudomonas poae* novel bacterial strain EY were equivalent to the control (FIG. 8). The length of the roots of inoculated with the *Pseudomonas poae* novel bacterial strain EY were significantly shorter than the control (FIG. 9).

Example 9—in Planta Inoculations Supporting Colonisation and Localisation of the *Pseudomonas poae* Novel Bacterial Strain EY in Wheat and Perennial Ryegrass Strain-specific primers were designed for *Pseudomonas poae* novel bacterial strain EY targeting the 3440768-3441879 bp region of the genome, which related to an insertion the paoA gene of the poaeamide biosynthetic gene cluster of EY (EY-F TGTTAAACACGCAACTCGCC; (SEQ ID NO. 4) EY-R AAAGGTGCACT-CACAACCTCTG; (SEQ ID NO 5) 5'→3'). An in silico analysis using Primer-BLAST indicated that the primers were strain-specific.

The strain-specific primer for EY was evaluated on cultures of strains *Pseudomonas poae* novel bacterial strain EY, along with closely related strains (DP, HC, CT14). Initially, bacterial cultures were grown in nutrient broth (BD Bioscience) and grown overnight at 22° C. in the dark in a shaking incubator. The Promega Wizard® genomic DNA purification kit was used with the following modifications: initial centrifugation of 1 mL of overnight culture at 13,000-16,000×g for 2 mins was performed twice to pellet bacterial cells; incubations were conducted at −20° C. for 10 mins to enhance protein precipitation; DNA pellets were rehydrated in 50 mL rehydration solution at 65° C. for 10 mins followed by overnight incubation at 4° C. Final DNA concentration was measured using a Quantus™ Fluorometer and stored at 4° C. until further processing. The 25 µL reaction mixture contained: 12.5 µL of OneTaq™ Hot Start 2×master mix with standard buffer (New England BioLabs®), 2 µL of each primer (10 µM/µL), 8.5 µL of nuclease-free water and 2 µL of template DNA sample. The thermocycling conditions were: initial denaturation at 94° C. for 1 min, followed by 30 cycles of denaturation at 94° C. for 30 sec, annealing at 58° C. for 1 min, elongation at 72° C. for 2 min, and a final extension at 72° C. for 10 min. PCR products were separated at 120 V in a 2% (w/v) agarose gel containing 0.05 µL mL−1 SYBR safe stain in 1 xTAE running buffer and visualized under UV light next to a 2 kb DNA ladder. The strain-specific primer generated an amplicon of the correct size (1112 bp) for *Pseudomonas poae* novel bacterial strain EY and DP (likely duplicate of EY) (FIG. 10).

The strain-specific primer for EY was evaluated on wheat plants inoculated with *Pseudomonas poae* novel bacterial strain EY. Initially, wheat seeds were sterilized in 70% ethanol for 3 minutes, followed by rinsing with sterilized distilled water (SDW) for three times. The bacterial strain was cultured in nutrient broth (BD Bioscience) overnight, while seeds were imbibed in nutrient broth overnight in the dark. Seeds and the bacterial culture were combined for 4 hours in dark in a shaking incubator. For the controls, seeds were not inoculated with bacteria. A total of three seeds were sown per pot into potting mix and grown in a glasshouse. For wheat, plants were harvested at only one time point (7 days after planting, DAP). For wheat inoculated with EY 10 replicates were maintained. For the uninoculated control treatments (wheat) 5 replicates were maintained for each time point. At harvest, plants were uprooted, washed thoroughly (roots only) and then sectioned into roots, pseudostem and leaves (wheat—7 DAP). Each section comprised three pieces (~0.5 cm$^2$) of plant tissue, which was placed into collection microtubes (2 mL) and stored at −80° C. The Qiagen® MagAttract® 96 DNA plant core kit (Qiagen®, Hilden, Germany) was utilized to extract plant DNA using the Biomek® FXP lab automation workstation linked to Biomek software version v. 4.1 and Gen 5 (v. 2.08) software (Biotek Instruments, USA) with the following modifications to the manufacturer's instructions: to each well of the 96 well microplate, a 33 µL aliquot of RB buffer and 10 µL of resuspended MegAttract suspension G was added. A touch-down PCR (TD-PCR) was performed to enhance the sensitivity and specificity of primers in planta, compared to in vitro pure cultures. The PCR reaction mixture was prepared as per in vitro cultures. Touch-down PCR amplification was performed in two phases. In phase I, initial denaturation was carried out at 94° C. for 1 min, followed by 10 cycles of denaturation at 94° C. for 30 sec, annealing for at 65-55° C. (dropping 1 C for each cycle) and 72° C. for 2 mins. In phase II, it was 20 cycles of denaturation at 94° C. for 30 sec, annealing at 58° C. for 1 min and extension at 72° C. for 2 min, with a final extension at 72° C. for 10 min. For wheat, the presence of the *Pseudomonas poae* novel bacterial strain EY was detected at 7 DAP, with the highest rates of incidence recorded in roots (80%), followed by pseudostem (30%), however it was not detected in the leaves (0%) (Table 9). Overall, *Pseudomonas poae* novel bacterial strain EY appears to inoculate into wheat, where it colonises subterranean and aerial tissue, but appears to preferentially colonise roots.

TABLE 9

Incidence of *Pseudomonas poae* novel bacterial strain EY in wheat at one harvest time point. The incidence is indicated as the number of plants showing the presence of EY per total number of replicates inoculated or uninoculated (R - roots; P - pseudostem; L - leaves).

|  | 7 DAP | | |
| --- | --- | --- | --- |
|  | R | P | L |
| EY | 8/10 | 3/10 | 0/10 |
| Control | 0/5 | 0/5 | 0/5 |

Example 10—in Planta Inoculations Supporting the Biofertilizer (Nitrogen) Niche of the *Pseudomonas poae* Novel Bacterial Strain EY An in planta biofertilizer assay was established in barley to evaluate the ability of *Pseudomonas poae* novel bacterial strain EY to aid growth under nitrogen limiting conditions. Initially, bacterial strains (5, including EY were cultured in 20 mL nutrient broth (BD Bioscience) overnight at 26° C. whilst rotating at 200 RPM. The following day cultures were pelleted via centrifugation at 4000 RPM for 5 minutes, washed three times in 10 mL Phosphate Buffered Saline (PBS), resuspended in 20 mL PBS, quantified via spectrophotometry (OD600) and diluted (1:10). Barley seeds were sterilized in 70% ethanol for 5 minutes, followed by rinsing with sterilized distilled water (SDW) for five times. These sterile seeds were submerged in the dilution for 4 hours in a dark incubator at room temperature whilst rotating at 200 RPM. The seeds were subsequently transferred to moistened sterile filter paper and allowed to germinate for three days. The three-day-old seedlings were individually transferred to 60 mm plates with semi-solid Burks media (HiMedia) (5 g/L Agar). Seedlings were allowed to grow for a further 4 days, before the shoots and roots were measured for each seedling. There was a total of 6 treatments (5 bacterial strains including EY; 1 blank media control) containing 10 seedlings per treatment. Statistical analysis (One-way ANOVA and Tukey Test) was conducted using OriginPro 2018 (Version b9.5.1.195) to detect the presence of any significant difference ($P<0.05$) between treatments.

The root growth of seedlings inoculated with novel bacterial strain EY and grown under nitrogen limiting conditions was significantly greater than the control ($P<0.05$), with an average increase of 28.6% (FIG. 11). The shoot growth of seedlings inoculated with novel bacterial strain EY was not significantly greater than the control ($P<0.05$), despite increasing shoot growth by 12.5% (FIG. 12). Overall, results indicate that novel bacterial strain EY can aid in the growth of seedlings grown under nitrogen limiting conditions.

Example 11—in Planta Inoculations Supporting the Biofertilizer (Phosphate Solubilisation) Niche of the *Pseudomonas poae* Novel Bacterial Strain EY An in planta biofertilizer assay was established in barley to evaluate the ability of *Pseudomonas poae* novel bacterial strain EY to aid growth under conditions with insoluble phosphate. Initially, bacterial strains (5, including EY) were cultured in 30 mL R2B overnight at 26° C. whilst rotating at 200 RPM. The following day the barley seeds were sterilized in 70% ethanol for 5 minutes, followed by rinsing with SDW for five times. These sterile seeds were submerged in the overnight cultures for 4 hours in a dark incubator at room temperature whilst rotating at 200 RPM. The seeds were subsequently transferred to moistened sterile filter paper to be allowed to germinate for three days. These three-day-old seedlings were individually transferred to 60 mm plates with semi-solid Pikovskaya media which contains yeast extract (0.5 g/L), D-glucose (5.0 g/L), calcium phosphate (5.0 g/L), ammonium sulphate (0.5 g/L), potassium chloride (0.2 g/L), magnesium sulphate (0.1 g/L), manganese sulphate (0.1 mg/L), ferrous sulphate (0.1 mg/L) and agar (5.0 g/L). These seedlings were allowed to grow for another 4 days, before the shoots and roots were measured for each seedling. There was a total of 6 treatments (5 bacterial strains including EY; 1 blank media control) containing 10 seedlings per treatment. Statistical analysis (One-way ANOVA and Tukey Test) was conducted using OriginPro 2018 (Version b9.5.1.195) to detect the presence of any significant difference ($P<0.05$) between treatments.

The root growth of seedlings inoculated with novel bacterial strain EY and grown under conditions with insoluble phosphate was significantly greater than the control ($P<0.05$), with an average increase of 62.5% (FIG. 13). The shoot growth of seedlings inoculated with novel bacterial strain EY was significantly greater than the control ($P<0.05$), with an average increase of 46.2 (FIG. 14). Overall, results indicate that novel bacterial strain EY can aid in the growth of seedlings grown under conditions with insoluble phosphate.

Example 12—in Planta Inoculations Identifying Optimal Concentrations of *Pseudomonas poae* Novel Bacterial Strain EY An in planta biofertilizer assay was established in perennial ryegrass to evaluate the optimal concentration in which *Pseudomonas poae* novel bacterial strain EY would support seedling growth. Initially, the bacterial strain was cultured overnight in 20 mL nutrient broth (BD Bioscience) at 26° C. whilst rotating at 200 RPM. The following day the culture was pelleted via centrifugation at 4000 RPM for 5 minutes, washed three times in 10 mL PBS, resuspended in 20 mL PBS, quantified via spectrophotometry (OD600). The culture was diluted (1:10) twice to create three concentrations ($10^0$, $10^{-1}$ and $10^{-2}$). The perennial ryegrass seeds were sterilized in 70% ethanol for 5 minutes, followed by rinsing five times with SDW. These sterile seeds were submerged in the dilutions for 4 hours in a dark incubator at room temperature whilst rotating at 200 RPM. After inoculation, 10 seeds were transferred to moistened sterile filter paper for germination from each dilution. After seven days, the roots and shoots were measured.

Root growth of seedlings inoculated with novel bacterial strain EY was greatest with the $10^{-1}$ dilution, which was 4.4% greater than $10^{-2}$ dilution and 14.0% greater than the $10^{-0}$ dilution (FIG. 15). Shoot growth of seedlings inoculated with novel bacterial strain EY was greatest with the $10^{-2}$ dilution, which was 13.3% greater than $10^{-1}$ dilution and 16.7% greater than the $10^{-0}$ dilution. Overall, results indicate that novel bacterial strain EY has the greatest effects on root and shoot growth at lower concentrations.

It is to be understood that various alterations, modifications and/or additions may be made without departing from the spirit of the present invention as outlined herein.

As used herein, except where the context requires otherwise, the term "comprise" and variations of the term, such as "comprising", "comprises" and "comprised", are not intended to be in any way limiting or to exclude further additives, components, integers or steps.

Reference to any prior art in the specification is not, and should not be taken as, an acknowledgment or any form of suggestion that this prior art forms part of the common general knowledge in Australia or any other jurisdiction or that this prior art could reasonably be expected to be combined by a person skilled in the art.

REFERENCES

1. Ankenbrand, M J, Hohlfeld, S, Hackl, T & Förster, F 2017, 'AliTV—interactive visualization of whole genome comparisons', *PeerJ Computer Science*, vol. 3.
2. Bolger, A M, Lohse, M & Usadel, B 2014, 'Trimmomatic: a flexible trimmer for Illumina sequence data', *Bioinformatics*, vol. 30, no. 15, pp. 2114-20.
3. Chun, J, Oren, A, Ventosa, A, Christensen, H, Arahal, D R, da Costa, M S, Rooney, A P, Yi, H, Xu, X W, De Meyer, S & Trujillo, M E 2018, 'Proposed minimal standards for the use of genome data for the taxonomy of prokaryotes', *Int J Syst Evol Microbiol*, vol. 68, no. 1, pp. 461-6.
4. De Coster, W, D'Hert, S, Schultz, D T, Cruts, M & Van Broeckhoven, C 2018, 'NanoPack: visualizing and processing long read sequencing data', *Bioinformatics*.
5. Henry, E, Toruño, T Y, Jauneau, A, Deslandes, L & Coaker, G 2017, 'Direct and indirect visualization of bacterial effector delivery into diverse plant cell types during infection', *The Plant Cell*, vol. 29, no. 7, pp. 1555-70.
6. Li, H 2018, 'Minimap2: pairwise alignment for nucleotide sequences', *Bioinformatics*, pp. bty191-bty.
7. Lindeberg, M, Cunnac, S & Collmer, A 2012, '*Pseudomonas syringae* type III effector repertoires: last words in endless arguments', *Trends Microbiol*, vol. 20, no. 4, pp. 199-208.
8. Lõytynoja, A 2014, 'Phylogeny-aware alignment with PRANK', in D J Russell (ed.), *Multiple Sequence Alignment Methods*, Humana Press, Totowa, NJ, pp. 155-70, DOI 10.1007/978-1-62703-646-7_10, <https://doi.org/10.1007/978-1-62703-646-7_10>.
9. Müller, H, Zachow, C, Alavi, M, Tilcher, R, Krempl, P M, Thallinger, G G & Berg, G 2013, 'Complete Genome Sequence of the Sugar Beet Endophyte *Pseudomonas poae* RE*1-1-14, a Disease-Suppressive Bacterium', *Genome Announc*, vol. 1, no. 2, p. e0002013.
10. Page, A J, Cummins, C A, Hunt, M, Wong, V K, Reuter, S, Holden, M T, Fookes, M, Falush, D, Keane, J A & Parkhill, J 2015, 'Roary: rapid large-scale prokaryote pan genome analysis', *Bioinformatics*, vol. 31, no. 22, pp. 3691-3.
11. Price, M N, Dehal, P S & Arkin, A P 2010, 'FastTree 2—approximately maximum-likelihood trees for large alignments', *PLoS One*, vol. 5, no. 3, p. e9490.
12. Richter, M & Rosselló-Móra, R 2009, 'Shifting the genomic gold standard for the prokaryotic species definition', *Proceedings of the National Academy of Sciences*, vol. 106, no. 45, pp. 19126-31.
13. Rodriguez, H & Fraga, R 1999, 'Phosphate solubilizing bacteria and their role in plant growth promotion', *Biotechnology Advances*, vol. 17, no. 4-5, pp. 319-39.
14. Seemann, T 2014, 'Prokka: rapid prokaryotic genome annotation', *Bioinformatics*, vol. 30, no. 14, pp. 2068-9.
15. Sharma, S, Kumar, V & Tripathi, R B 2017, 'Isolation of phosphate solubilizing microorganism (PSMs) from soil', *Journal of microbiology and Biotechnology Research*, vol. 1, no. 2, pp. 90-5.
16. Sundar ORacand, W & Sinha, M 1963, 'Phosphate dissolving microorganisms in the rhizosphere and soil', *Indiaj Agric Sci*, vol. 33, no. 7, pp. 272-8.
17. Tallapragada, P & Seshachala, U 2012, 'Phosphate-solubilizing microbes and their occurrence in the rhizospheres of *Piper betel* in Karnataka, India', *Turkish Journal of Biology*, vol. 36, no. 1, pp. 25-35.
18. Vaser, R, Sovic, I, Nagarajan, N & Sikic, M 2017, 'Fast and accurate de novo genome assembly from long uncorrected reads', *Genome Res*, vol. 27, no. 5, pp. 737-46.
19. Walker, B J, Abeel, T, Shea, T, Priest, M, Abouelliel, A, Sakthikumar, S, Cuomo, C A, Zeng, Q, Wortman, J, Young, S K & Earl, A M 2014, 'Pilon: an integrated tool for comprehensive microbial variant detection and genome assembly improvement', *PLoS One*, vol. 9, no. 11, p. e112963.
20. Weber, T, Blin, K, Duddela, S, Krug, D, Kim, H U, Bruccoleri, R, Lee, S Y, Fischbach, M A, Muller, R, Wohlleben, W, Breitling, R, Takano, E & Medema, M H 2015, 'antiSMASH 3.0—a comprehensive resource for the genome mining of biosynthetic gene clusters', *Nucleic Acids Res*, vol. 43, no. W1, pp. W237-43.
21. Wei, H-L, Zhang, W & Collmer, A 2018, 'Modular study of the type III effector repertoire in *Pseudomonas syringae* pv. tomato DC3000 reveals a matrix of effector interplay in pathogenesis', *Cell reports*, vol. 23, no. 6, pp. 1630-8.
22. Wick, R R, Judd, L M, Gorrie, C L & Holt, K E 2017, 'Unicycler: Resolving bacterial genome assemblies from short and long sequencing reads', *PLOS Computational Biology*, vol. 13, no. 6, p. e1005595.
23. Wick, R R, Schultz, M B, Zobel, J & Holt, K E 2015, 'Bandage: interactive visualization of de novo genome assemblies', *Bioinformatics*, vol. 31, no. 20, pp. 3350-2.

The invention claimed is:

1. A purified or isolated endophyte strain, wherein said endophyte is a strain of *Pseudomonas poae* which provides bioprotection and/or biofertilizer phenotypes to plants into which it is inoculated and is *Pseudomonas poae* strain EY as deposited with The National Measurement Institute on 17th May 2019 with accession number V19/009907.

2. The endophyte according to claim 1, wherein the bioprotection and/or biofertilizer phenotype includes production of a bioprotectant compound in the plant into which the endophyte is inoculated.

3. The endophyte according to claim 2, wherein the bioprotectant compound is poaeamide or a derivative, isomer and/or salt thereof.

4. The endophyte according to claim 1, wherein the bioprotection and/or biofertilizer phenotype is selected from the group consisting of production of organic acids, solubilisation of phosphate and nitrogen fixation in the plant into which the endophyte is inoculated.

5. A plant or part thereof inoculated with one or more endophytes according to claim 1, wherein the plant into which the endophyte is inoculated is an endophyte-free host plant or part thereof and is stably infected with said endophyte.

6. A method for producing a bioprotectant compound, or a derivative, isomer and/or a salt thereof, said method including infecting a plant with the endophyte according to claim 1 and cultivating the plant under conditions suitable to produce the bioprotectant compound; or
said method including culturing the endophyte according to claim 1 under conditions suitable to produce the bioprotectant compound; and
optionally isolating the bioprotectant compound from the plant or culture medium.

7. The method according to claim 6, wherein the conditions include a culture medium including a source of carbohydrates.

8. A method of providing bioprotection to a plant against bacterial and/or fungal pathogens and/or providing biofertilizer to a plant, said method including infecting the plant with the endophyte according to claim 1 and cultivating the plant.

9. The method according to claim 8, wherein the method includes providing bioprotection to the plant and includes production of a bioprotectant compound in the plant into which the endophyte is inoculated; or
wherein the method includes providing biofertilizer to the plant and includes production of organic acids, increased phosphate use efficiency, increased solubilisation of phosphate, increased nitrogen use efficiency and/or increased nitrogen availability, in the plant into which the endophyte is inoculated; or
wherein the method includes increasing phosphate use efficiency or increasing phosphate solubilisation in the plant, and wherein the plant is cultivated in the presence of soil phosphate and/or applied phosphate; or
wherein the method includes increasing nitrogen use efficiency or nitrogen availability, and
wherein the plant is cultivated in a low nitrogen medium.

10. A method of increasing phosphate use efficiency or increasing phosphate solubilisation by a plant, said method including infecting the plant with the endophyte according to claim 1, and cultivating the plant.

11. The method according to claim 10, wherein the plant is cultivated in the presence of soil phosphate and/or applied phosphate.

12. A method of growing a plant in a low nitrogen medium, said method including infecting the plant with the bioprotectant compound-producing endophyte according to claim 1, and cultivating the plant.

13. The method according to claim 12, wherein the plant is cultivated in soil.

14. The plant according to claim 5 which is an agricultural plant species selected from one or more of forage grass, turf grass, bioenergy grass, grain crop and industrial crop.

15. The plant according to claim 5 which is selected from the group consisting of:
a forage, turf or bioenergy grass selected from the group consisting of those belonging to the genera *Lolium* and *Festuca*, including *L. perenne* (perennial ryegrass), *L. arundinaceum* (tall fescue) and *L. multiflorum* (Italian ryegrass), and those belonging to the *Brachiaria-Urochloa* species complex (panic grasses), including *Brachiaria brizantha, Brachiaria decumbens, Brachiaria humidicola, Brachiaria stolonifera, Brachiaria ruziziensis, B. dictyoneura, Urochloa brizantha, Urochloa decumbens, Urochloa humidicola, Urochloa mosambicensis* and interspecific and intraspecific hybrids of *Brachiaria-Urochloa* species complex; or
is a grain crop or industrial crop selected from the group consisting of those belonging to the genus *Triticum*, including *T. aestivum* (wheat), those belonging to the genus *Hordeum*, including *H. vulgare* (barley), those belonging to the genus *Avena*, including *A. sativa* (oats), those belonging to the genus *Zea*, including *Z. mays* (maize or corn), those belonging to the genus *Oryza*, including *O. sativa* (rice), those belonging to the genus *Saccharum* including *S. officinarum* (sugarcane), those belonging to the genus Sorghum including *S. bicolor* (sorghum), those belonging to the genus *Panicum*, including *P. virgatum* (switchgrass), those belonging to the genera *Miscanthus, Paspalum, Pennisetum, Poa, Eragrostis* and *Agrostis*; or
is a grain crop or industrial crop selected from the group consisting of wheat, barley, oats, chickpeas, triticale, fava beans, lupins, field peas, canola, cereal rye, vetch, lentils, millet/panicum, safflower, linseed, sorghum, sunflower, maize, canola, mungbeans, soybeans, and cotton.

16. The method of claim 7, wherein the source of carbohydrates is selected from one or more of the group consisting of a starch/sugar-based agar or broth, a cereal-based agar or broth, endophyte agar, Murashige and Skoog with 20% sucrose, half V8 juice/half PDA, water agar and yeast malt extract agar.

17. The method of claim 9, wherein the bioprotectant compound is poaeamide or a derivative, isomer and/or salt thereof.

18. The method of claim 9, wherein the applied phosphate includes phosphate applied by fertilizer.

19. The method of claim 9, wherein the low nitrogen medium is low nitrogen soil.

20. The method of claim 11, wherein the applied phosphate includes phosphate applied by fertilizer and wherein the plant is cultivated in soil.

* * * * *